United States Patent [19]

Wepplo

[11] Patent Number: 5,523,278
[45] Date of Patent: Jun. 4, 1996

[54] SUBSTITUTED BENZISOXAZOLE AND BENZISOTHIAZOLE HERBICIDAL AGENTS

[75] Inventor: Peter J. Wepplo, Princeton, N.J.

[73] Assignee: American Cyanamid Company, Madison, N.J.

[21] Appl. No.: 526,911

[22] Filed: Sep. 12, 1995

Related U.S. Application Data

[62] Division of Ser. No. 387,143, Feb. 10, 1995, Pat. No. 5,484,763.

[51] Int. Cl.$^6$ .......................... A01N 43/80; C07D 413/04
[52] U.S. Cl. .......................... 504/271; 548/108; 548/241; 548/126; 548/136; 548/144; 548/184; 548/228; 548/227; 548/128; 548/131; 544/182; 544/238; 544/310; 504/191; 504/265; 504/263; 504/238; 504/243; 504/229
[58] Field of Search .......................... 548/241, 126, 548/136, 144, 184, 228, 227, 128, 131; 544/182, 238, 310; 504/191, 271, 265, 263, 238, 243, 229

[56] References Cited

U.S. PATENT DOCUMENTS 5,298,520  3/1994  Baker et al. .......................... 514/383

5,451,588  9/1995  Baker et al. .......................... 514/323

FOREIGN PATENT DOCUMENTS

| 665226 | 8/1995 | European Pat. Off. | |
| 93/20066 | 10/1993 | WIPO . | |
| WO93/23396 | 11/1993 | WIPO .......................... | C07D 471/04 |
| WO94/02477 | 2/1994 | WIPO .......................... | C07D 403/14 |

*Primary Examiner*—Johann Richter
*Assistant Examiner*—Laura R. Cross
*Attorney, Agent, or Firm*—Joseph M. Mazzarese

[57] ABSTRACT

There are provided substituted benzisoxazole and benzisothiazole compounds having the structural formula I

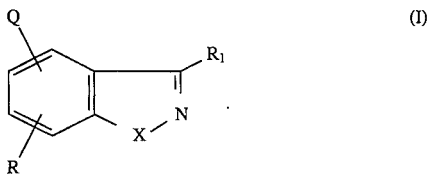

Further provided are compositions and methods comprising those compounds for the control of undesirable plant species.

7 Claims, No Drawings

SUBSTITUTED BENZISOXAZOLE AND BENZISOTHIAZOLE HERBICIDAL AGENTS

This is a divisional of application Ser. No. 08/387,143, filed on Feb. 10, 1995, now U.S. Pat. No. 5,484,763.

BACKGROUND OF THE INVENTION

Weeds cause tremendous global economic losses by reducing crop yields and lowering crop quality. In the United States alone, agronomic crops must compete with hundreds of weed species.

In spite of the commercial herbicides available today, damage to crops caused by weeds still occurs. Accordingly, there is ongoing research to create new and more effective herbicides.

Certain benzisoxazole and benzisothiazole compounds are known to have herbicidal or auxin-like activity (U.S. Pat. No. 3,657,263; EP 442655-A2; E. Chrystal, T. Cromartie, R. Ellis and M. Battersby, Proceedings of the Brighton Crop Protection Conference—Weeds, 1, pp. 189–194 (1993); K. Sato, T. Honma and S. Sugai, Journal of Agricultural and Biological Chemistry, 49, pp. 3563–3567 (1985); and M. Giannella, F. Gualtieri and C. Melchiorre, Phytochemistry, 10 pp. 539–544 (1971)). However, none of those publications describe the herbicidal agents of the present invention.

U.S. Pat. No. 4,844,728 describes certain pyrazole-1,2-benzisothiazole and -benzisoxazole compounds which are used as intermediates in the preparation of pyrazole-sulfonamide herbicidal agents. However, the compounds of the present invention are not specifically described in that patent and no herbicidal activity is disclosed for those intermediate compounds.

It is therefore an object of the present invention to provide compounds which are highly effective for controlling undesirable plant species.

It is also an object of the present invention to provide methods for controlling undesirable plant species.

These and other objects of the present invention will become more apparent from the detailed description thereof set forth below.

SUMMARY OF THE INVENTION

The present invention describes substituted benzisoxazole and benzisothiazole compounds which are useful as herbicidal agents.

The substituted benzisoxazole and benzisothiazole compounds of the present invention have the structural formula I

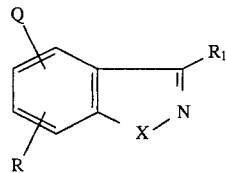

(I)

wherein

R is hydrogen, halogen, $C_1$–$C_4$alkyl, $C_1$–$C_4$haloalkyl, $C_1$–$C_4$alkoxy or $C_1$–$C_4$haloalkoxy;

$R_1$ is halogen, $X_1R_2$ or $R_2$;

X and $X_1$ are each independently O or S;

$R_2$ is hydrogen, $C_1$–$C_4$alkyl optionally substituted with one to three halogen atoms, one to three $C_1$–$C_4$alkoxy groups, one to three $C_1$–$C_4$alkylthio groups, one cyano group, one $COR_3$ group, one $CO_2R_4$ group, one $CONR_5R_6$ group or one phenyl group optionally substituted with one to three halogen atoms, one to three $C_1$–$C_4$alkyl groups, one to three $C_1$–$C_4$alkoxy groups, one $C_3$–$C_6$cycloalkyl group, one $C_1$–$C_4$haloalkyl group, one $C_1$–$C_4$alkylthio group, one cyano group, one nitro group, one $COR_7$ group, one $CO_2R_8$ group or one $OR_9$ group, $C_3$–$C_7$cycloalkyl optionally substituted with one to three halogen atoms, one to three $C_1$–$C_4$alkoxy groups, one to three $C_1$–$C_4$alkylthio groups, one cyano group, one $COR_3$ group, one $CO_2R_4$ group, one $CONR_5R_6$ group or one phenyl group optionally substituted with one to three halogen atoms, one to three $C_1$–$C_4$alkyl groups, one to three $C_1$–$C_4$alkoxy groups, one $C_3$–$C_6$cycloalkyl group, one $C_1$–$C_4$haloalkyl group, one $C_1$–$C_4$alkylthio group, one cyano group, one nitro group, one $COR_7$ group, one $CO_2R_8$ group or one $OR_9$ group, $C_2$–$C_6$alkenyl optionally substituted with one to three halogen atoms, one to three $C_1$–$C_4$alkoxy groups, one to three $C_1$–$C_4$alkylthio groups, one cyano group, one $COR_3$ group, one $CO_2R_4$ group, one $CONR_5R_6$ group or one phenyl group optionally substituted with one to three halogen atoms, one to three $C_1$–$C_4$alkyl groups, one to three $C_1$–$C_4$alkoxy groups, one $C_3$–$C_6$cycloalkyl group, one $C_1$–$C_4$haloalkyl group, one $C_1$–$C_4$alkylthio group, one cyano group, one nitro group, one $COR_7$ group, one $CO_2R_8$ group or one $OR_9$ group, $C_4$–$C_7$cycloalkenyl optionally substituted with one to three halogen atoms, one to three $C_1$–$C_4$alkoxy groups, one to three $C_1$–$C_4$alkylthio groups, one cyano group, one $COR_3$ group, one $CO_2R_4$ group, one $CONR_5R_6$ group or one phenyl group optionally substituted with one to three halogen atoms, one to three $C_1$–$C_4$alkyl groups, one to three $C_1$–$C_4$alkoxy groups, one $C_3$–$C_6$cycloalkyl group, one $C_1$–$C_4$haloalkyl group, one $C_1$–$C_4$alkylthio group, one cyano group, one nitro group, one $COR_7$ group, one $CO_2R_8$ group or one $OR_9$ group, $C_2$–$C_6$alkynyl optionally substituted with one to three halogen atoms, one to three $C_1$–$C_4$alkoxy groups, one to three $C_1$–$C_4$alkylthio groups, one cyano group, one $COR_3$ group, one $CO_2R_4$ group, one $CONR_5R_6$ group or one phenyl group optionally substituted with one to three halogen atoms, one to three $C_1$–$C_4$alkyl groups, one to three $C_1$–$C_4$alkoxy groups, one $C_3$–$C_6$cycloalkyl group, one $C_1$–$C_4$haloalkyl group, one $C_1$–$C_4$alkylthio group, one cyano group, one nitro group, one $COR_7$ group, one $CO_2R_8$ group or one $OR_9$ group, or phenyl optionally substituted with one to three halogen atoms, one to three $C_1$–$C_4$alkyl groups, one to three $C_1$–$C_4$alkoxy groups, one $C_3$–$C_6$cycloalkyl group, one $C_1$–$C_4$haloalkyl group, one $C_1$–$C_4$alkylthio group, one cyano group, one nitro group, one $COR_3$ group, one $CO_2R_4$ group or one $OR_9$ group;

$R_3$, $R_5$, $R_6$ and $R_7$ are each independently hydrogen, $C_1$–$C_4$alkyl, $C_2$–$C_4$alkenyl, $C_2$–$C_4$alkynyl, benzyl or phenyl;

$R_9$ is $C_1$–$C_4$alkyl substituted with one $CO_2R_{10}$ group;

$R_4$, $R_8$ and $R_{10}$ are each independently hydrogen, $C_1$–$C_4$alkyl, $C_2$–$C_4$alkenyl, $C_2$–$C_4$alkynyl, benzyl, phenyl or an alkali metal, alkaline earth metal, manganese, copper, zinc, cobalt, silver or nickel cation;
Q is selected from
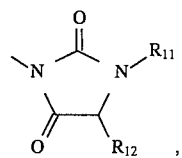 Q1
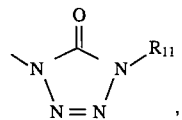 Q2
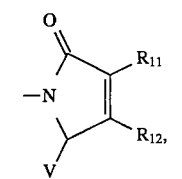 Q3
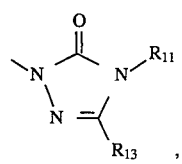 Q4
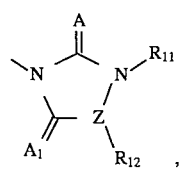 Q5
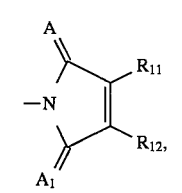 Q6
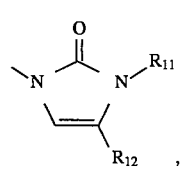 Q7
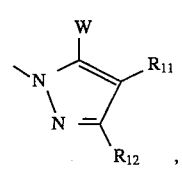 Q8
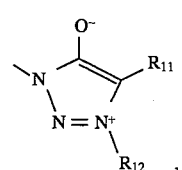 Q9
-continued
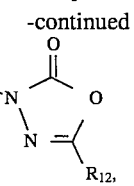 Q10
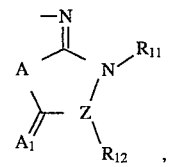 Q11
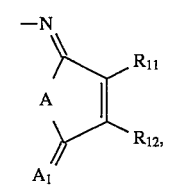 Q12
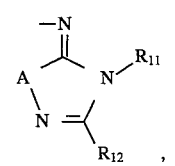 Q13
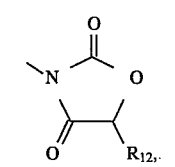 Q14
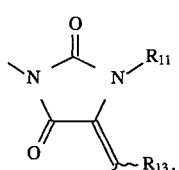 Q15
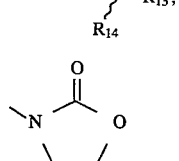 Q16
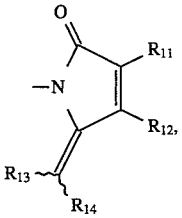 Q17
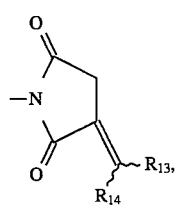 Q18

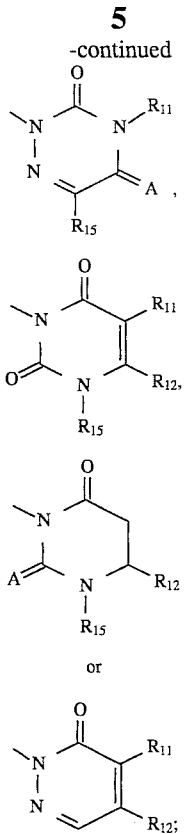

R₁₁ and R₁₂ are each independently hydrogen,
C₁–C₆alkyl optionally substituted with one or more halogen atoms, or
C₃–C₆cycloalkyl optionally substituted with one or more halogen atoms, and
when R₁₁ and R₁₂ are taken together with the atoms to which they are attached, they represent a four- to seven-membered saturated or unsaturated ring optionally interrupted by O, S or N, and optionally substituted with one to three methyl groups or one or more halogen atoms;

R₁₃, R₁₄ and R₁₅ are each independently hydrogen or C₁–C₃alkyl;

A and A₁ are each independently O or S;

V is hydroxy, halogen, C₁–C₃alkoxy or C₁–C₃alkylthio;

W is halogen or C₁–C₃alkyl; and

Z is N or CH.

This invention also relates to compositions containing those compounds and methods for using those compounds and compositions. Advantageously, it has been found that the compounds of the present invention, and compositions containing them, are useful for the control of undesirable plant species. The compounds of the present invention are especially useful for the post-emergence control of undesirable plant species.

DETAILED DESCRIPTION OF THE INVENTION

The present invention provides a method for controlling undesirable plant species which comprises applying to the foliage of said plants or to the soil or water containing seeds or other propagating organs thereof, a herbicidally effective amount of a formula I, substituted benzisoxazole or benzisothiazole compound.

The present invention also provides a method for the control of undesirable plant species in transplanted rice which comprises applying to the soil or water containing seeds or other propagating organs of said undesirable plant species, after the rice has been transplanted, a herbicidally effective amount of a formula I, substituted benzisoxazole or benzisothiazole compound.

The substituted benzisoxazole and benzisothiazole compounds of the present invention have the structural formula I

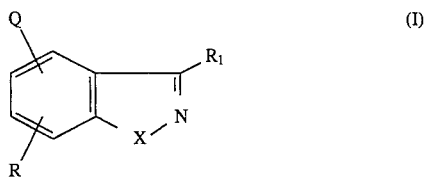

wherein

R, R₁, X and Q are as described above.

Preferred formula I substituted benzisoxazole and benzisothiazole compounds of this invention are those wherein R is hydrogen, halogen, C₁–C₄alkyl, C₁–C₄haloalkyl, C₁–C₄alkoxy or C₁–C₄haloalkoxy;

R₁ is halogen, X₁R₂ or R₂;

X is O or S;

X₁ is O;

R₂ is hydrogen,
C₁–C₄alkyl optionally substituted with one C₁–C₄alkoxy, C₁–C₄alkylthio or CO₂R₄ group,
C₃–C₆cycloalkyl optionally substituted with one C₁–C₄alkoxy, C₁–C₄alkylthio or CO₂R₄ group,
C₃–C₆alkenyl,
C₃–C₆alkynyl, or
phenyl optionally substituted with one to three halogen atoms, one C₁–C₄alkoxy group, one C₁–C₄alkylthio group or one OR₉ group;

R₉ is C₁–C₄alkyl substituted with one CO₂R₁₀ group;

R₄ and R₁₀ are each independently hydrogen or C₁–C₄alkyl;

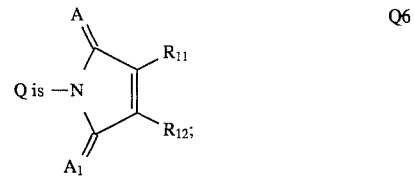

R₁₁ and R₁₂ are each independently hydrogen,
C₁–C₆alkyl optionally substituted with one or more halogen atoms,
C₃–C₆cycloalkyl optionally substituted with one or more halogen atoms, and
when R₁₁ and R₁₂ are taken together with the atoms to which they are attached, they may form a ring in which R₁₁R₁₂ is a C₂–C₅alkylene group optionally substituted with one to three methyl groups or one or more halogen atoms; and A and A₁ are each independently O or S.

More preferred formula I herbicidal agents of the present invention are those having the structural formula II

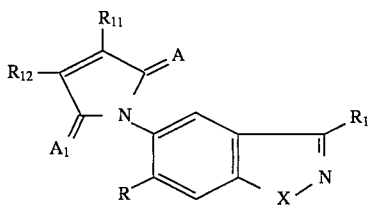

(II)

wherein

R is hydrogen, halogen, $C_1$–$C_4$alkyl, $C_1$–$C_4$haloalkyl, $C_1$–$C_4$alkoxy or $C_1$–$C_4$haloalkoxy;

$R_1$ is halogen, $X_1R_2$ or $R_2$;

X is O or S;

$X_1$ is O;

$R_2$ is hydrogen,
 $C_1$–$C_4$alkyl optionally substituted with one $C_1$–$C_4$alkoxy, $C_1$–$C_4$alkylthio or $CO_2R_4$ group,
 $C_3$–$C_6$cycloalkyl optionally substituted with one $C_1$–$C_4$alkoxy, $C_1$–$C_4$alkylthio or $CO_2R_4$ group,
 $C_3$–$C_6$alkenyl,
 $C_3$–$C_6$alkynyl, or
 phenyl optionally substituted with one to three halogen atoms, one $C_1$–$C_4$alkoxy group, one $C_1$–$C_4$alkylthio group or one $OR_9$ group;

$R_9$ is $C_1$–$C_4$alkyl substituted with one $CO_2R_{10}$ group;

$R_4$ and $R_{10}$ are each independently hydrogen or $C_1$–$C_4$alkyl;

Q is 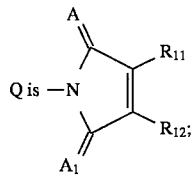 Q6

$R_{11}$ and $R_{12}$ are each independently hydrogen,
 $C_1$–$C_6$alkyl optionally substituted with one or more halogen atoms,
 $C_3$–$C_6$cycloalkyl optionally substituted with one or more halogen atoms, and
 when $R_{11}$ and $R_{12}$ are taken together with the atoms to which they are attached, they may form a ring in which $R_{11}R_{12}$ is a $C_2$–$C_5$alkylene group optionally substituted with one to three methyl groups or one or more halogen atoms; and A and $A_1$ are each independently O or S.

Another group of more preferred substituted benzisoxazole and benzisothiazole compounds of the present invention are those having the structural formula II wherein R is hydrogen or halogen;

$R_1$ is halogen, $X_1R_2$ or $R_2$;

X is O or S;

$X_1$ is O;

$R_2$ is hydrogen,
 $C_1$–$C_4$alkyl optionally substituted with one $CO_2R_4$ group,
 $C_3$–$C_4$alkenyl,
 $C_3$–$C_4$alkynyl, or
 phenyl optionally substituted with one $C_1$–$C_4$alkoxy group or one $OR_9$ group;

$R_9$ is $C_1$–$C_4$alkyl substituted with one $CO_2R_{10}$ group;

$R_{10}$ is $C_1$–$C_4$alkyl;

$R_{11}$ and $R_{12}$ are each independently $C_1$–$C_4$alkyl, and when $R_{11}$ and $R_{12}$ are taken together with the atoms to which they are attached, they may form a ring in which $R_{11}R_{12}$ is a $C_3$–$C_5$alkylene group optionally substituted with one to three methyl groups or one or more halogen atoms; and A and $A_1$ are O.

Most preferred herbicidal agents of this invention which are especially useful for the postemergence control of undesirable plant species are those having the structural formula II wherein R is hydrogen, F or Cl;

$R_1$ is halogen, $X_1R_2$ or $R_2$;

X is O or S;

$X_1$ is O;

$R_2$ is hydrogen,
 $C_1$–$C_4$alkyl optionally substituted with one $CO_2R_4$ group,
 $C_3$–$C_4$alkenyl,
 $C_3$–$C_4$alkynyl, or
 phenyl optionally substituted with one $C_1$–$C_4$alkoxy group or one $OR_9$ group;

$R_9$ is $C_1$–$C_4$alkyl substituted with one $CO_2R_{10}$ group;

$R_{10}$ is $C_1$–$C_4$alkyl;

$R_{11}$ and $R_{12}$ are each independently $C_1$–$C_4$alkyl, and when $R_{11}$ and $R_{12}$ are taken together with the atoms to which they are attached, they may form a ring in which $R_{11}R_{12}$ is a butylene group optionally substituted with one to three methyl groups or one or more halogen atoms; and A and $A_1$ are O.

Substituted benzisoxazole and benzisothiazole compounds of the present invention which are particularly effective herbicidal agents include methyl 5-(1-cyclohexene-1,2-dicarboximido)-α-methyl-1,2 -benzisothiazole-3-acetate; methyl 5-(1-cyclohexene-1,2-dicarboximido)-1,2-benzisothiazole-3-acetate; N-[3-(o-methoxyphenyl)-1,2-benzisothiazol-5-yl]-1 -cyclohexene-1,2-dicarboximide; N-(3-phenyl-1,2-benzisothiazol-5-yl)-1-cyclohexene-1,2 -dicarboximide; N-(1,2-benzisothiazol-5-yl)-1-cyclohexene-1,2-dicarboximide; methyl 5-(1-cyclohexene-1,2-dicarboximido)-1,2 -benzisoxazole-3-acetate; methyl 5-(1-cyclohexene-1,2-dicarboximido)-6-fluoro-1,2 -benzisoxazole-3-acetate; methyl 5-(1-cyclohexene-1,2-dicarboximido)-6-fluoro-α-methyl-1,2-benzisoxazole-3-acetate; methyl 5-(3, 4-dimethyl-2,5-dioxo-3-pyrrolin-1-yl)-6 -fluoro-α-methyl-1,2-benzisoxazole-3-acetate; N-[3-(allyloxy)-1,2-benzisoxazol-5-yl]-1-cyclohexene-1,2-dicarboximide; and methyl 2-{[6-chloro-5-(1-cyclohexene-1,2-dicarboximido)-1,2-benzisoxazol-3-yl]oxy}propionate, among others.

Exemplary of halogen hereinabove are fluorine, chlorine, bromine and iodine. The terms "$C_1$–$C_4$haloalkyl" and "$C_1$–$C_4$haloalkoxy" are defined as a $C_1$–$C_4$alkyl group or a $C_1$–$C_4$alkoxy group substituted with one or more halogen atoms, respectively. In formula I above, alkali metals include: sodium, potassium and lithium. Further, alkaline earth metals of formula I include magnesium and calcium.

It has been found that the compounds of the present invention are especially useful for the postemergence control of undesirable plant species.

Certain compounds of the present invention wherein Q is Q1 may be prepared by converting an aminobenzisoxazole or aminobenzisothiazole of formula III to its corresponding isocyanate of formula IV using standard methods such as phosgene in an inert solvent or palladium chloride and carbon monoxide. The formula IV compound is then treated with an amino acid of formula V, an amino ester of formula VI in the presence of triethylamine followed by treatment of the intermediate urea of formula VII with ethanolic hydrogen chloride, or an α-bromocarboxamide of formula VIII in the presence of a base such as potassium t-butoxide to form the desired compound. The above reactions are shown below in Flow Diagram I.

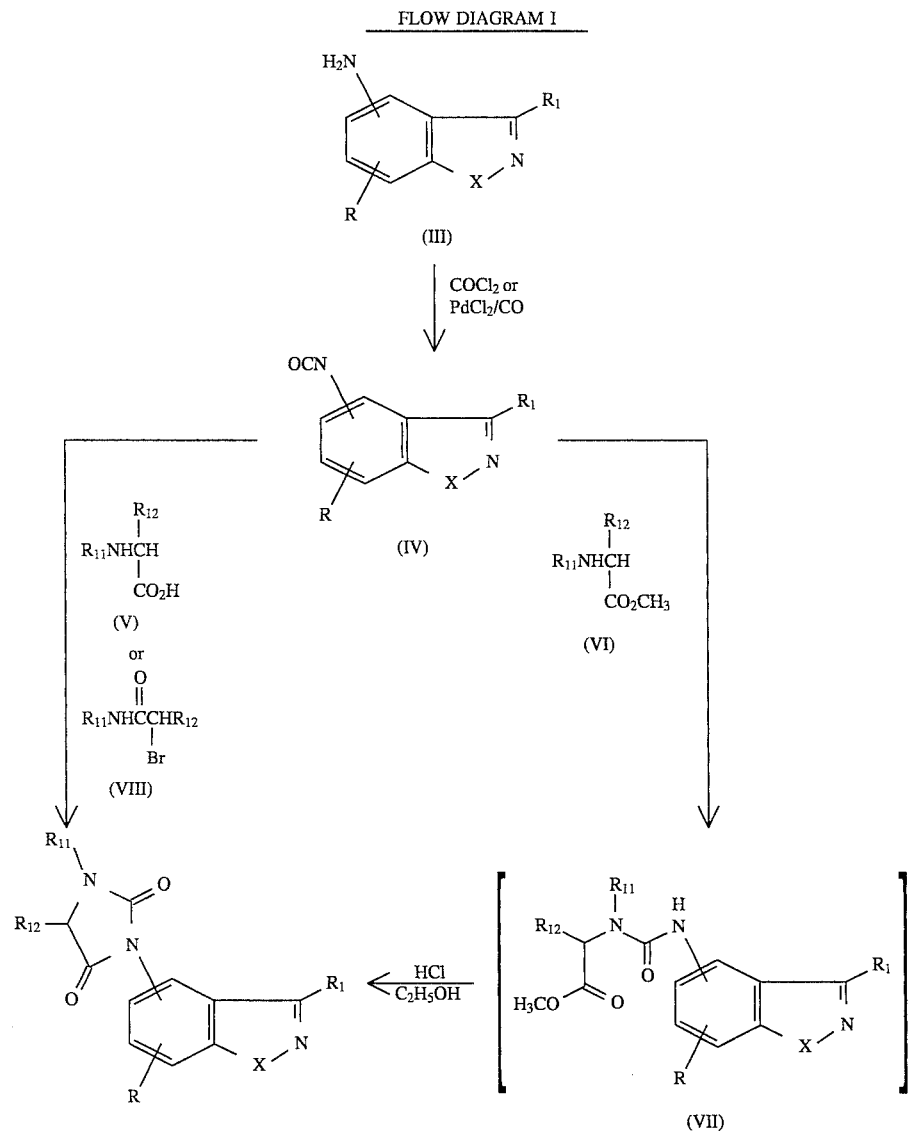

Compounds of formula I wherein Q is Q2 may be prepared by converting an aminobenzisoxazole or aminobenzisothiazole of formula III to its corresponding azide of formula IX by treatment with sodium nitrite, sodium azide, acetic acid, hydrogen chloride and sodium acetate or with sodium nitrite, hydrazine hydrate and acetic acid. The formula IX compound is then treated with an isocyanate of formula X to form the desired product. The above reaction scheme is shown in Flow Diagram II.

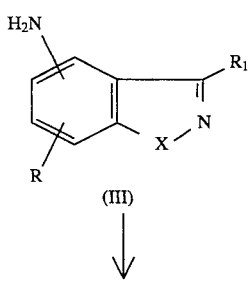

-continued
FLOW DIAGRAM II

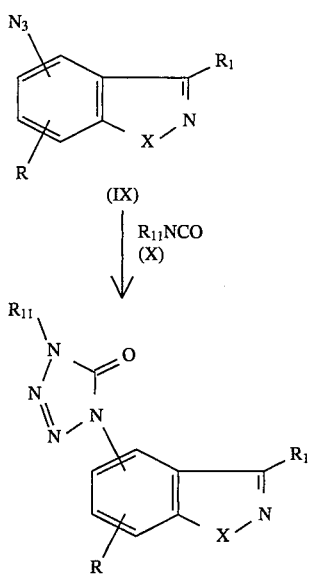

Alternatively, compounds of formula I wherein Q is Q2 may be prepared by reacting an isocyanate of formula IV with trimethyl silylazide to form a compound of formula XI and alkylating the formula XI compound by conventional means. The reactions are shown below in Flow Diagram III.

FLOW DIAGRAM III

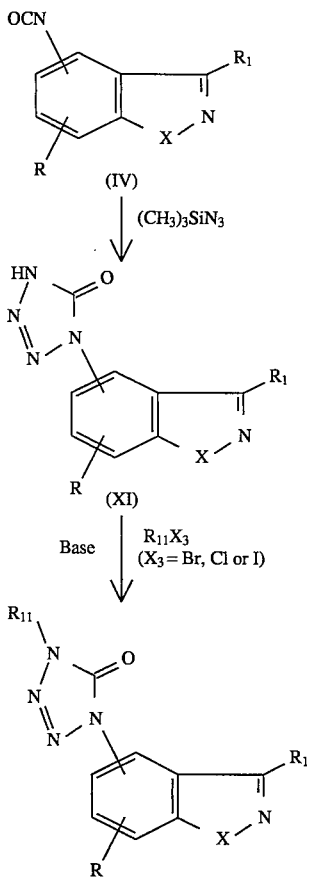

Formula I compounds wherein Q is Q6 and A and $A_1$ are may be prepared by reacting an aminobenzisoxazole or aminobenzisothiazole of formula III with an anhydride compound of formula XII, preferably at an elevated temperature. The reaction is shown in Flow Diagram IV.

FLOW DIAGRAM IV

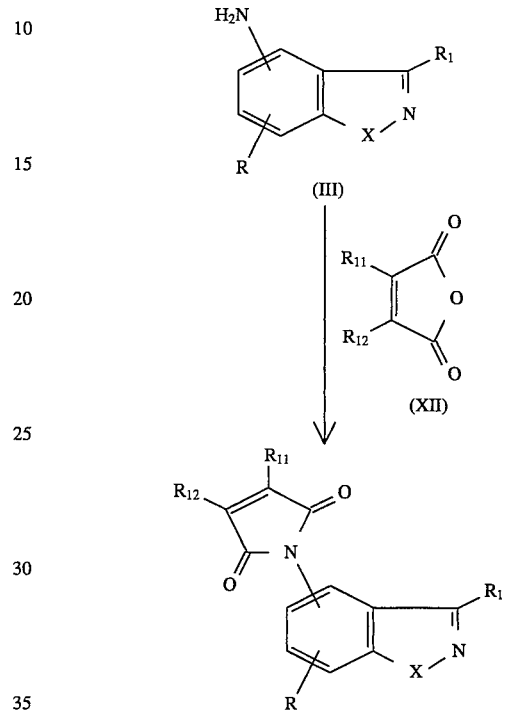

Formula I compounds wherein Q is Q6 and at least one of A or $A_1$ is S may be prepared by treating a formula I compound wherein Q is Q6 and A and $A_1$ are O with phosphorus pentasulfide or Lawesson's reagent (2,4-bis(4-methoxyphenyl)- 1,3-dithia-2,4-diphosphetane-2,4-disulfide) in an inert solvent such as toluene, xylene or chloroform.

Compounds of formula I wherein Q is Q3 may be prepared by reacting a compound of formula I wherein Q is Q6 and A and $A_1$ are O with sodium borohydride to form a compound wherein V is OH, reacting the compound wherein V is OH with a base and a suitable alkylating agent to form a compound wherein V is $C_1$–$C_3$alkoxy or reacting the compound wherein V is OH with a halogenating agent such as phosphorus trichloride, thionyl chloride, phosphorus tribromide, triphenyl phosphine-bromine, phosphorus triiodide or triphenyl phosphine-iodine in an inert solvent such as chloroform to form a compound wherein V is halogen and further reacting the compound wherein V is halogen with a $C_1$–$C_3$alkyl sulfide to form a compound wherein V is $C_1$–$C_3$alkylthio. The above reaction schemes are shown in Flow Diagram V.

FLOW DIAGRAM V

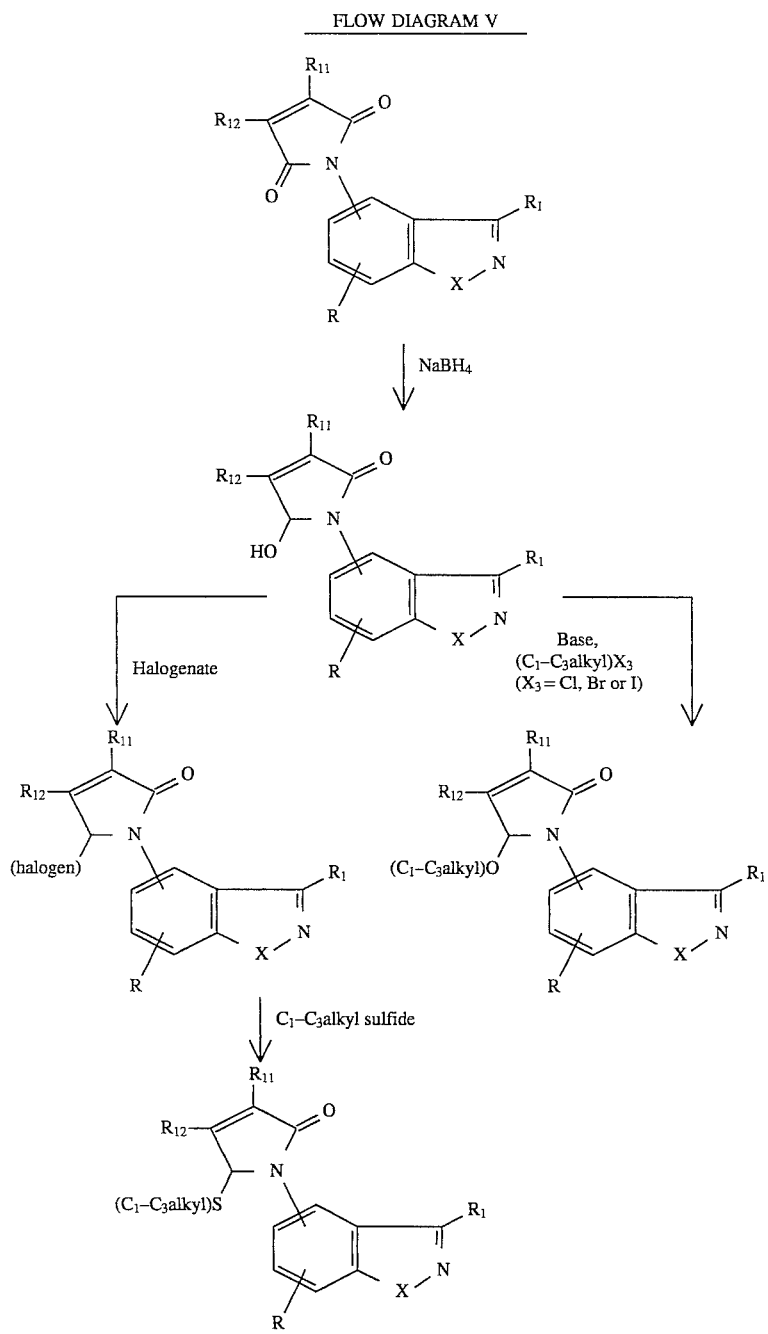

Formula I compounds wherein Q is Q5, Z is nitrogen and A and $A_1$ are oxygen may be prepared by reacting an isocyanate of formula IV with a substituted N-alkoxycarbonyl hydrazine of formula XII to form an intermediate compound and reacting the intermediate compound with a base to obtain the desired compound. The reaction scheme is shown in Flow Diagram VI.

FLOW DIAGRAM VI

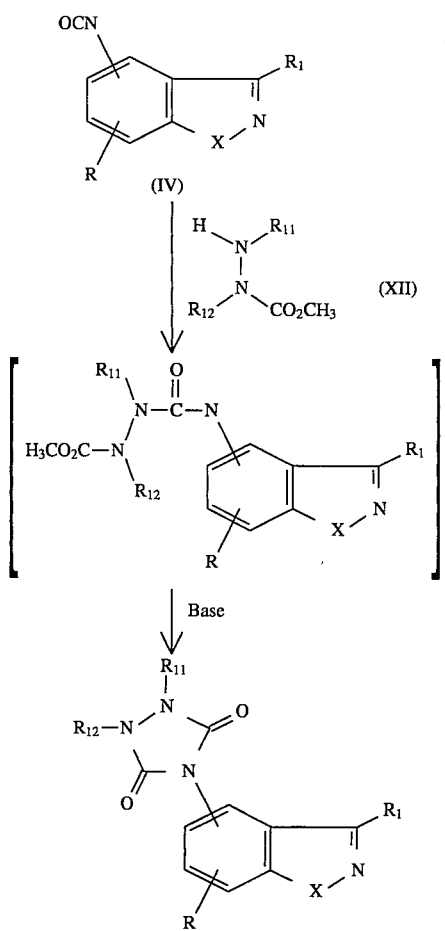

Similarly, formula I compounds wherein Q is Q5, Z is nitrogen, A is sulfur and $A_1$ is oxygen may be prepared by reacting an aminobenzisoxazole or aminobenzisothiazole of formula III with thiophosgene to form an isothiocyanate of formula XIII, reacting the isothiocyanate with a substituted N-alkoxycarbonyl hydrazine of formula XII to form an intermediate compound and reacting the intermediate compound with a base. The reaction scheme is shown below in Flow Diagram VII.

FLOW DIAGRAM VII

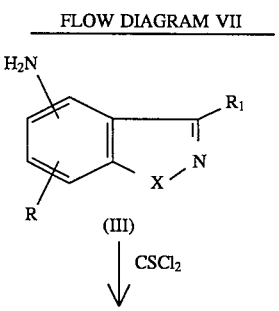

-continued
FLOW DIAGRAM VII

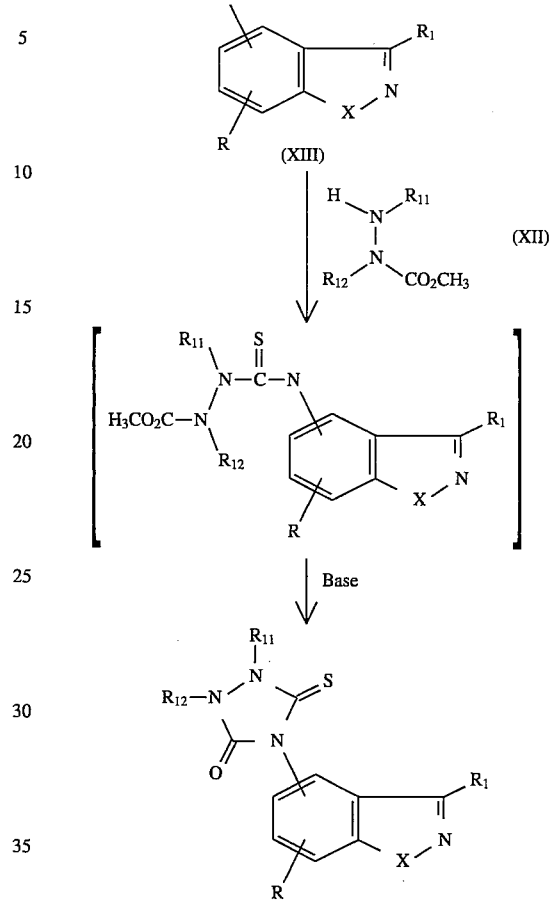

Compounds of formula I wherein Q is Q5, Z is carbon, A is sulfur and $A_1$ is oxygen may be prepared by reacting an isothiocyanate of formula XIII with an amino ester of formula VI in an inert solvent to form an intermediate, thiourea compound and treating the thiourea compound with ethanolic hydrogen chloride or base at an elevated temperature. The above reaction scheme is shown below in Flow Diagram VIII.

FLOW DIAGRAM VIII

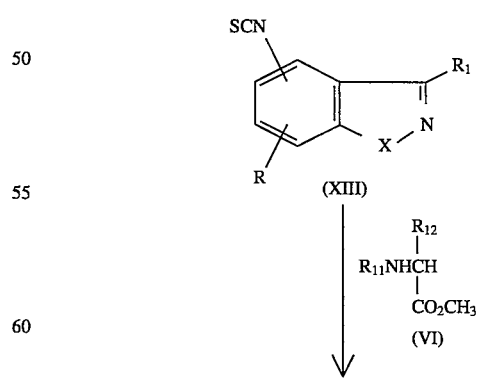

-continued
FLOW DIAGRAM VIII

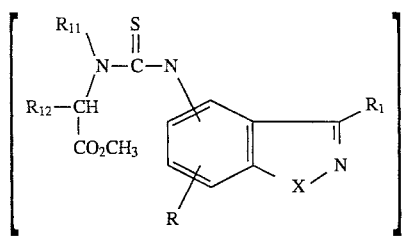

↓ C₂H₅OH/HCl or Base

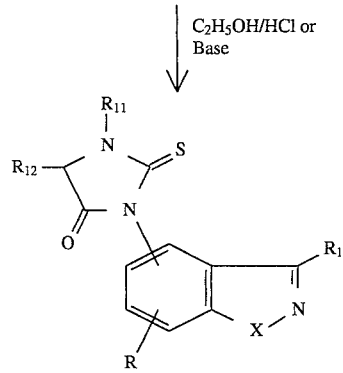

Formula I compounds wherein Q is Q5 and A and/or A₁ are sulfur may be prepared by treating a formula I compound wherein Q is Q5 and A and A₁ are oxygen with phosphorus pentasulfide or Lawesson's reagent (2,4-bis(4-methoxyphenyl)-1,3-dithia-2,4-diphosphetane-2,4-disulfide) in an inert solvent such as toluene, xylene or chloroform.

Formula I compounds wherein Q is Q4 may be prepared by diazotizing an aminobenzisoxazole or aminobenzisothiazole of formula III by standard methods to form an intermediate compound which is reduced with sodium sulfite to form a hydrazine of formula XIV. The hydrazine is then reacted with an imino-ester of formula XV to form an amidrazone of formula XVI and reacting the amidrazone with phosgene or a suitable phosgene equivalent optionally in the presence of triethylamine to form the desired compound. The reactions are shown in Flow Diagram IX.

FLOW DIAGRAM IX

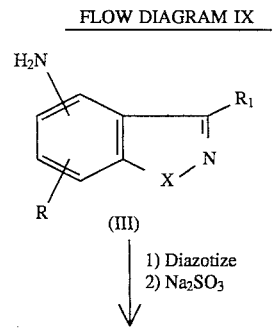

1) Diazotize
2) Na₂SO₃

↓

-continued
FLOW DIAGRAM IX

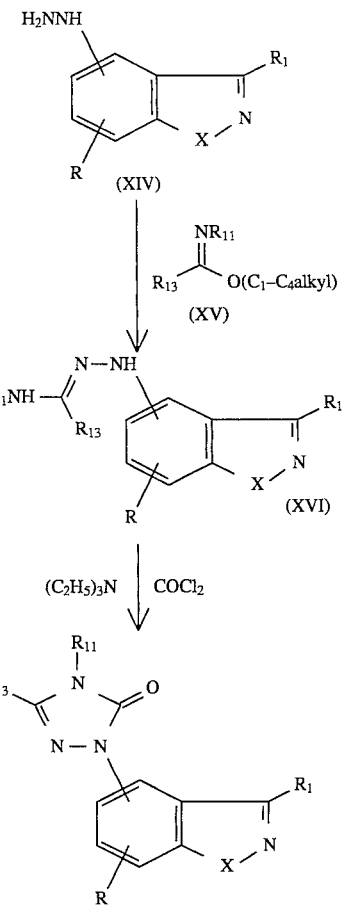

Compounds of formula I wherein Q is Q7 may be prepared by reacting an aminobenzisoxazole or aminobenziso-thiazole of formula III with a β-aminoaldehyde of formula XVII in the presence of a base in an inert solvent to form an intermediate compound and reacting the intermediate compound with phosgene or a phosgene equivalent. The above reaction scheme is shown in Flow Diagram X.

FLOW DIAGRAM X

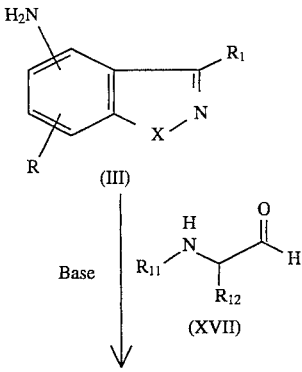

↓

-continued
FLOW DIAGRAM X

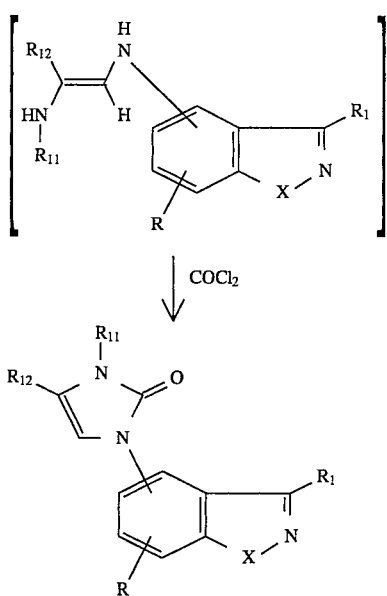

Formula I compounds wherein Q is Q8 and W is halogen may be prepared by reacting a hydrazine compound of formula XIV or its hydrochloride salt with a 2-alkoxycarbonylalkanone of formula XVIII optionally in the presence of a base such as triethylamine or sodium acetate in an inert solvent such as ethanol or toluene to form a 2,3-dihydropyrazol-3-one of formula XIX and halogenating the 2,3-dihydropyrazol-3-one with phosphorus oxychloride or phosphorus oxybromide. The reactions are shown in Flow Diagram XI.

FLOW DIAGRAM XI

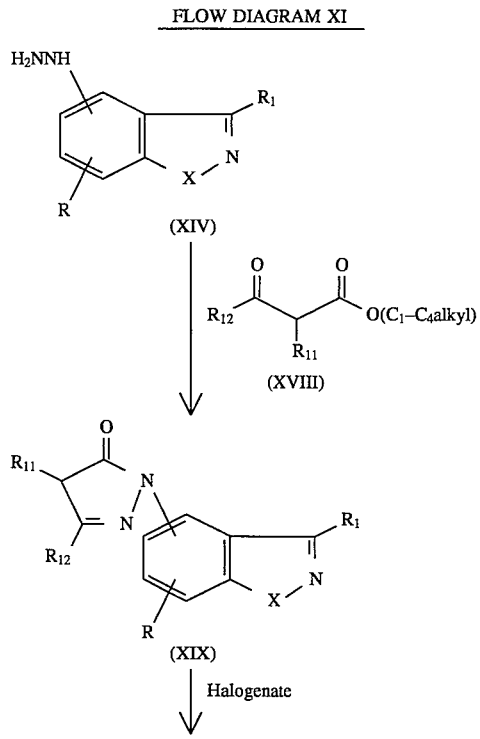

-continued
FLOW DIAGRAM XI

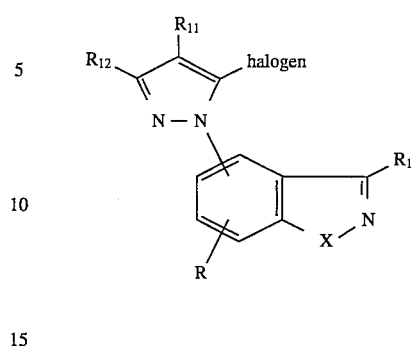

Formula I compounds wherein Q is Q8 and W is $C_1$–$C_3$alkyl may be prepared by reacting a hydrazine compound of formula XIV with a 1,3-diketone of formula XX optionally in the presence of a base in an inert solvent. The reaction is shown below in Flow Diagram XII.

FLOW DIAGRAM XII

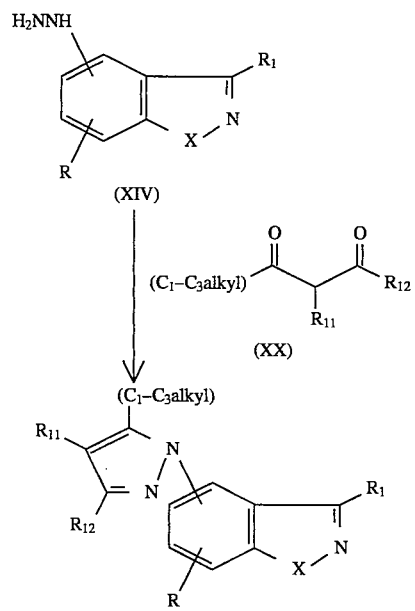

Formula I compounds wherein Q is Q9 may be prepared by diazotizing an aminobenzisoxazole or aminobenzisothiazole of formula III to form an intermediate diazonium salt and reacting the intermediate salt in situ with a β-aminoacid of formula XXI in the presence of triethylamine. The reaction scheme is shown below in Flow Diagram XIII.

FLOW DIAGRAM XIII

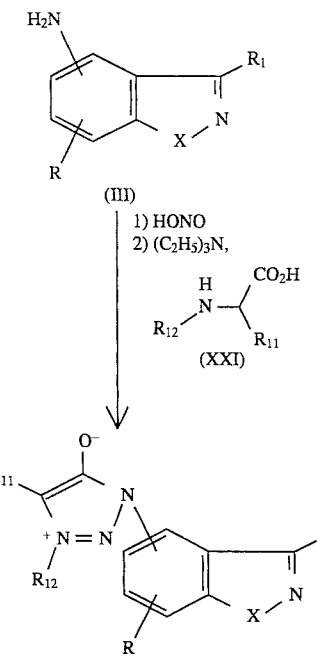

Compounds of formula I wherein Q is Q10 may be prepared by reacting a hydrazine of formula XIV with an acyl halide of formula XXII in the presence of a base such as triethylamine or pyridine to form an acyl hydrazide of formula XXIII and reacting the acyl hydrazide with trichloromethyl chloroformate, phosgene or a suitable phosgene equivalent optionally in the presence of triethylamine. The reaction scheme is shown below in Flow Diagram XIV.

FLOW DIAGRAM XIV

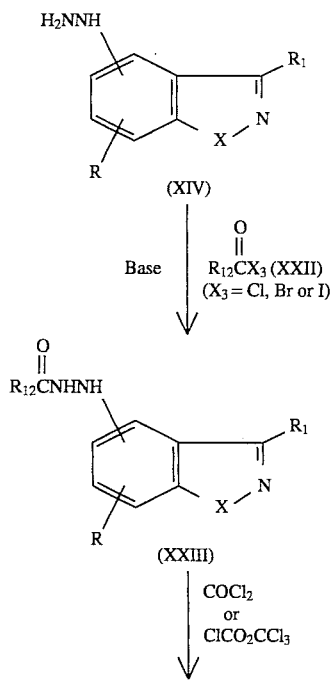

-continued
FLOW DIAGRAM XIV

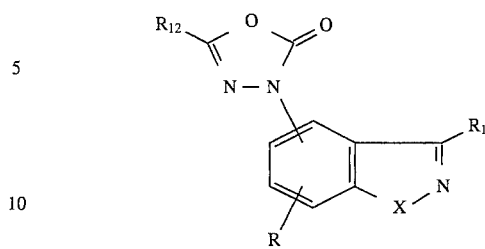

Formula I compounds wherein Q is Q11, A is sulfur, $A_1$ is oxygen and Z is CH may be prepared by reacting an isothiocyanate of formula XIII with an amine of formula XXIV to form a thiourea of formula XXV and reacting the thiourea with an α-halocarbonyl halide of formula XXVI in the presence of a base. The reactions are shown in Flow Diagram XV.

FLOW DIAGRAM XV

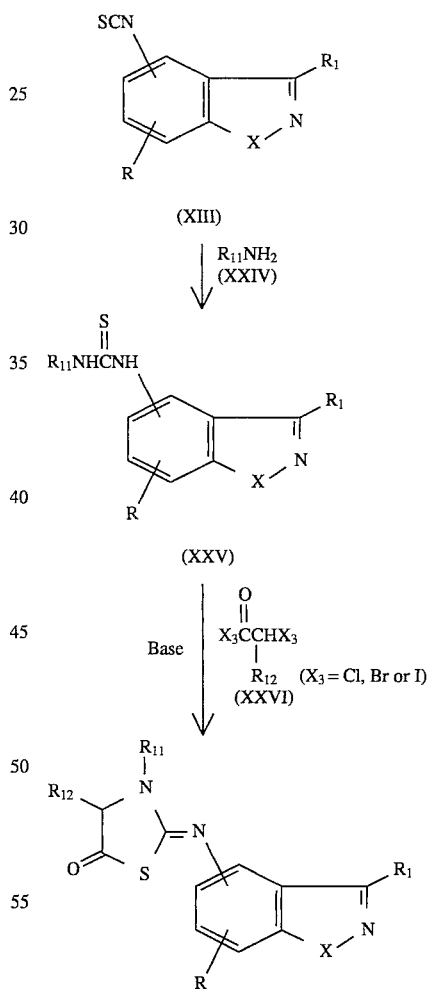

Formula I compounds wherein Q is Q11, A is sulfur, $A_1$ is oxygen and Z is nitrogen may be prepared by reacting an isothiocyanate of formula XIII with a substituted hydrazine of formula XXVII to form an intermediate compound of formula XXVIII and reacting the intermediate compound with phosgene or a suitable phosgene equivalent in the presence of a base such as triethylamine. The reaction sequence is shown in Flow Diagram XVI.

FLOW DIAGRAM XVI

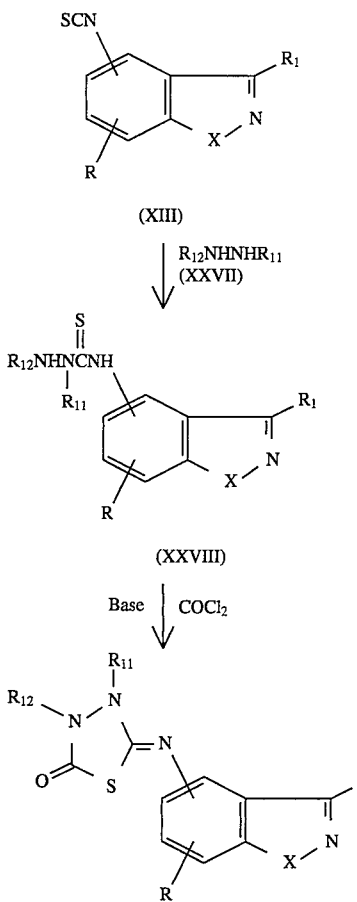

(XIII)

(XXVIII)

Compounds of formula I wherein Q is Q11, A and $A_1$ are oxygen and Z is CH may be prepared by reacting an isocyanate of formula IV with an amine of formula XXIV to form a urea of formula XXIX, dehydrating the urea to form a carbodiimide of formula XXX, reacting the carbodiimide with an α-halocarbonyl halide of formula XXVI to form a haloamidine of formula XXXI, hydrolyzing the haloamidine with aqueous acid to form an acylurea, heating the acylurea in situ to form an O-acylurea of formula XXXII and reacting the O-acylurea with a base such as triethylamine. The above reaction sequence is shown below in Flow Diagram XVII.

FLOW DIAGRAM XVII

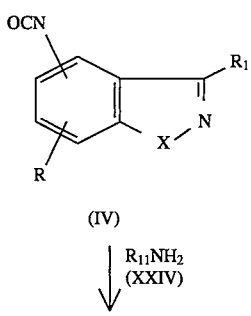

(IV)

FLOW DIAGRAM XVII -continued

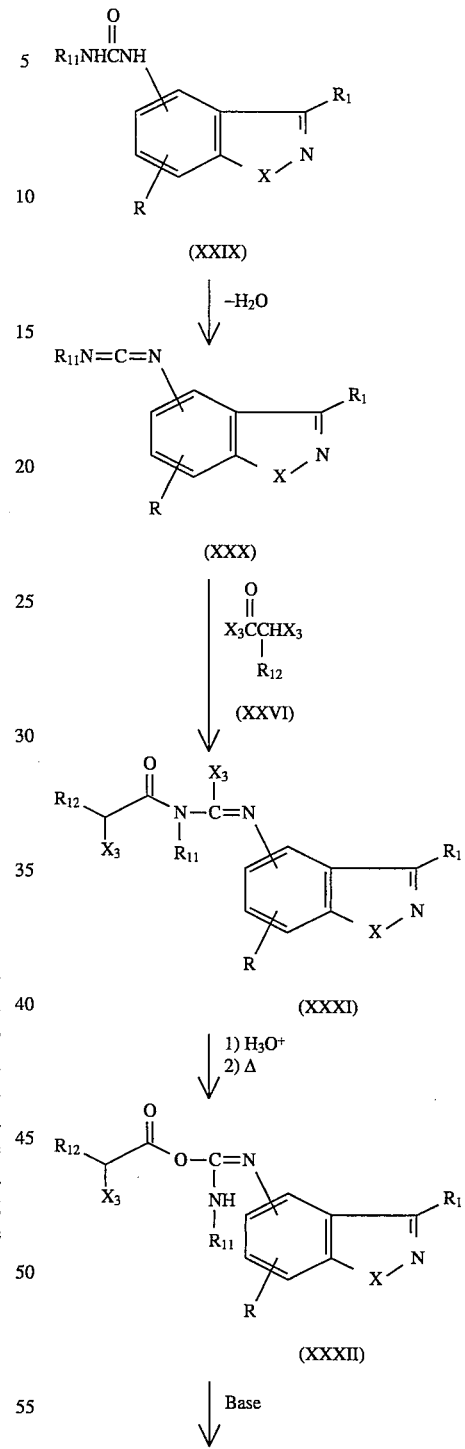

-continued
FLOW DIAGRAM XVII

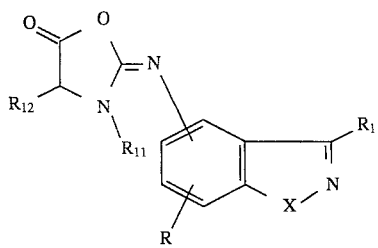

Formula I compounds wherein Q is Q12 and A and $A_1$ are oxygen may be prepared by reacting an aminobenzisoxazole or aminobenzisothiazole of formula III with an anhydride of formula XII to form an acid-amide of formula XXXIII and dehydrating the acid-amide with a dehydrating agent such as 1,3-dicyclohexylcarbodiimide. The reaction scheme is shown below in Flow Diagram XVIII.

FLOW DIAGRAM XVIII

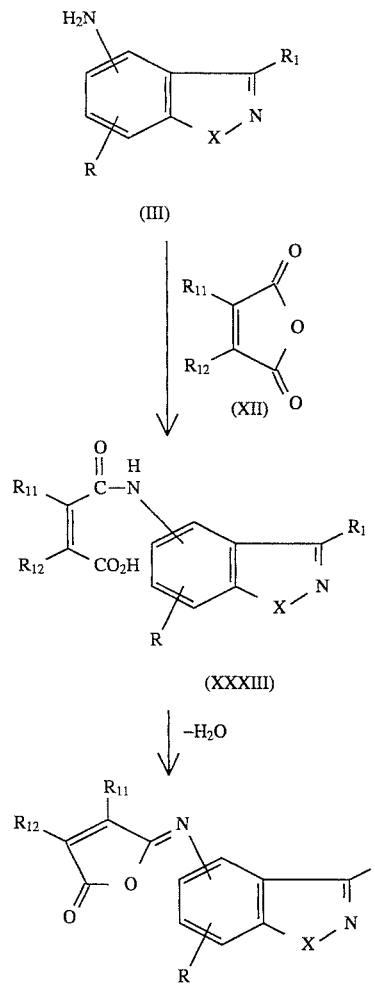

Compounds of formula I wherein Q is Q12, A is sulfur and $A_1$ is oxygen may be prepared by reacting an acid-amide of formula XXXIII with phosphorus pentasulfide or Lawesson's reagent followed by base to form an acid-thioamide of formula XXXIV and dehydrating the acid-thioamide with a dehydrating agent such as 1,3-dicyclohexylcarbodiimide. The reactions are shown in Flow Diagram XIX.

FLOW DIAGRAM XIX

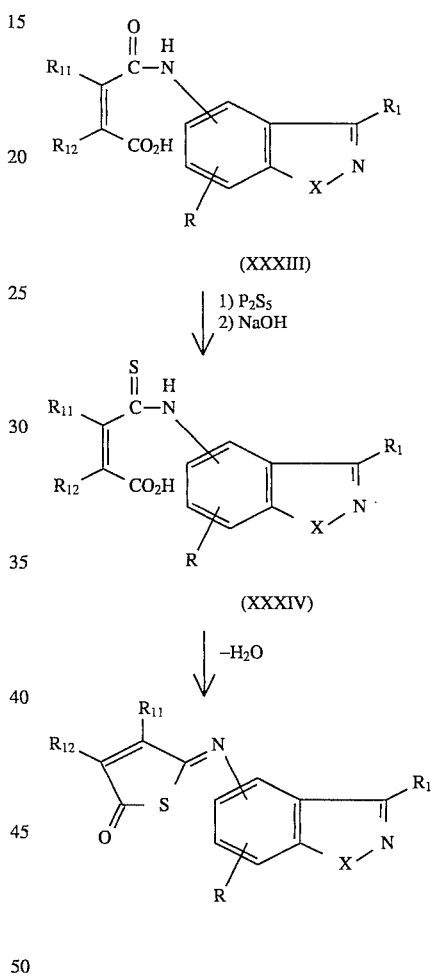

Certain formula I compounds wherein Q is Q13 may be prepared by reacting a thiourea of formula XXV with iodomethane to form an isothiourea of formula XXXV and reacting the isothiourea with a chloro-oxime of formula XXXVI. The reaction scheme is shown in Flow Diagram XX.

FLOW DIAGRAM XX

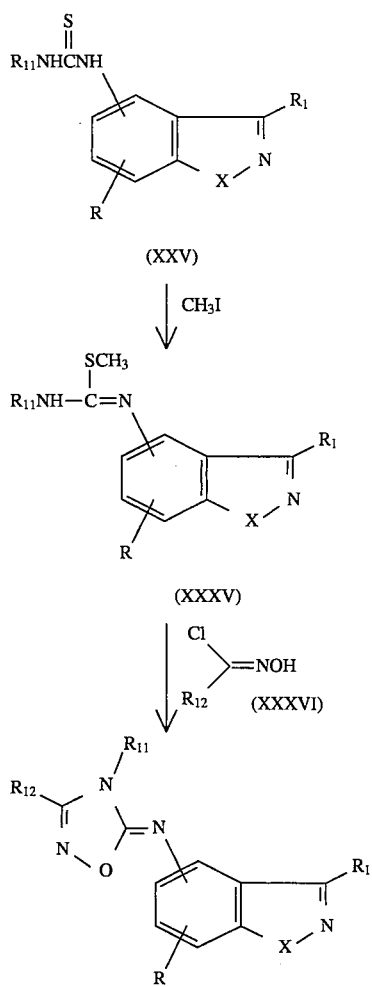

FLOW DIAGRAM XXI

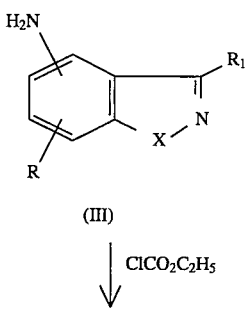

Compounds of formula I wherein Q is Q14 may be prepared by reacting an aminobenzisoxazole or aminobenzisothiazole of formula III with ethyl chloroformate to form a carbamate of formula XXXVII and reacting the carbamate with a hydroxy ester of formula XXXVIII at an elevated temperature with removal of ethanol. The reaction sequence is shown in Flow Diagram XXI.

-continued
FLOW DIAGRAM XXI

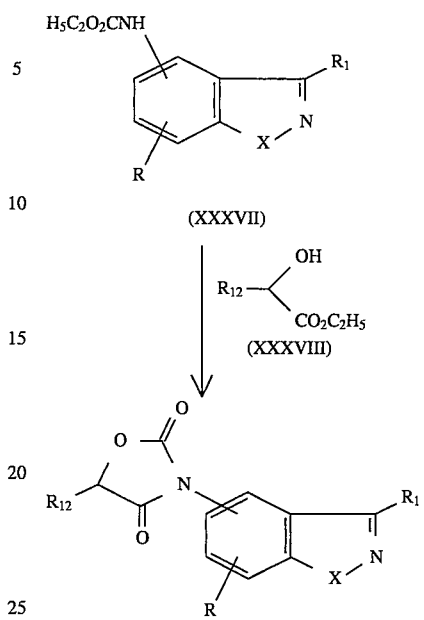

Alternatively, compounds of formula I wherein Q is Q14 may be prepared by reacting an isocyanate of formula IV with a hydroxy ester of formula XXXVIII to form an intermediate compound of formula XXXIX and reacting the intermediate compound with a base such as sodium acetate in an inert solvent such as toluene. The reaction scheme is shown below in Flow Diagram XXII.

FLOW DIAGRAM XXII

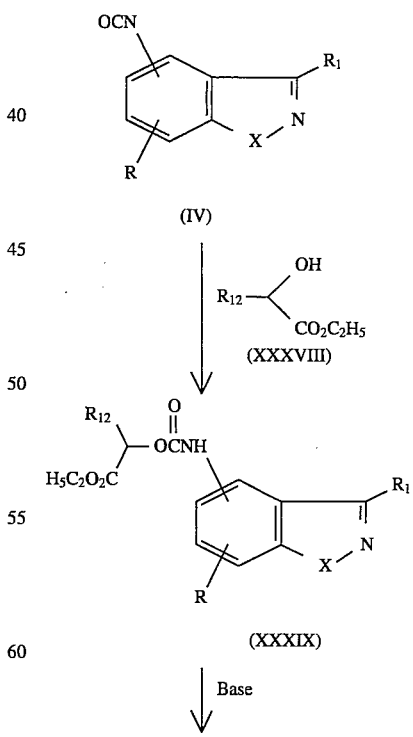

-continued
FLOW DIAGRAM XXII

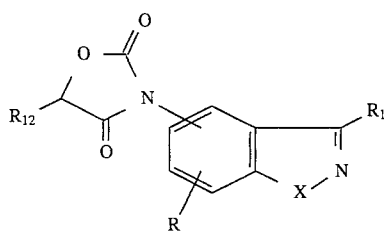

Formula I compounds wherein Q is Q15 may be prepared by reacting an isocyanate of formula IV with α-amino-α,β-unsaturated ester of formula XL to form a urea of formula XLI and reacting the urea with a base such as sodium acetate in an inert solvent such as toluene at an elevated temperature. The reactions are shown in Flow Diagram XXIII.

FLOW DIAGRAM XXIII

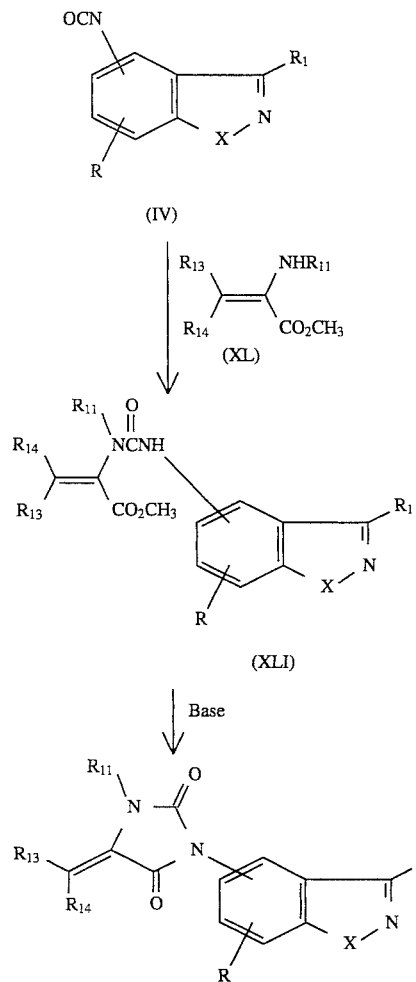

Alternatively, formula I compounds wherein Q is Q15 may be prepared by reacting an isocyanate of formula IV with an amino acid of formula XLII to form a urea of formula XLIII, reacting the urea with aqueous acid to form a hydantoin of formula XLIV and reacting the hydantoin with an acetal of formula XLV. The reaction scheme is shown below in Flow Diagram XXIV.

FLOW DIAGRAM XXIV

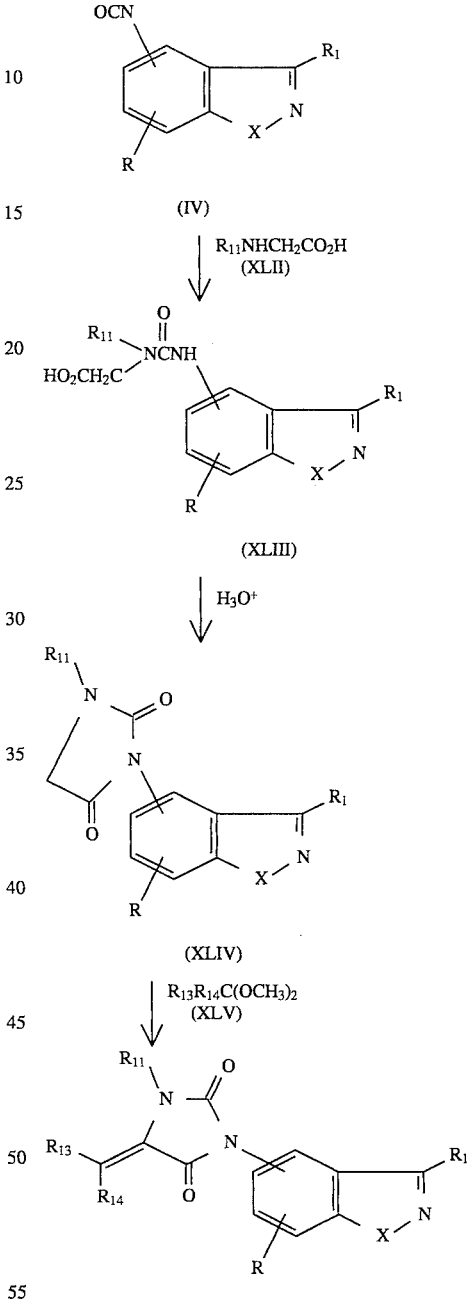

Compounds of formula I wherein Q is Q16 may be prepared by reacting an isocyanate of formula IV with a hydroxy alkenoate of formula XLVI in the presence of a base such as triethylamine. The reaction is shown in Flow Diagram XXV.

FLOW DIAGRAM XXV

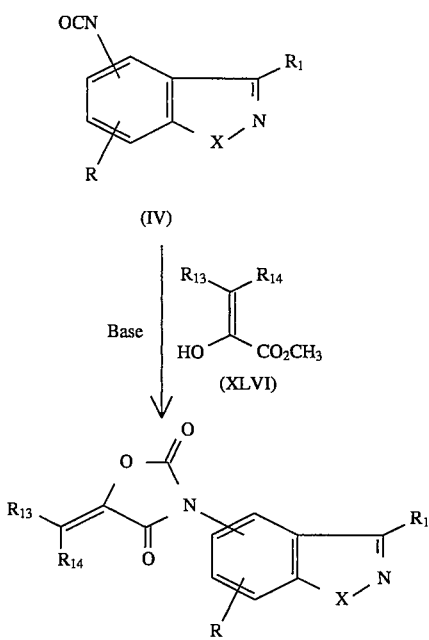

Formula I compounds wherein Q is Q17 may be prepared by reacting a formula I compound wherein Q is Q6 with a Grignard Reagent of formula XLVII in a solvent such as diethyl ether or tetrahydrofuran at an elevated temperature to form an intermediate compound of formula XLVIII and reacting the intermediate compound with potassium bisulfate at an elevated temperature. The reaction scheme is shown in Flow Diagram XXVI.

FLOW DIAGRAM XXVI

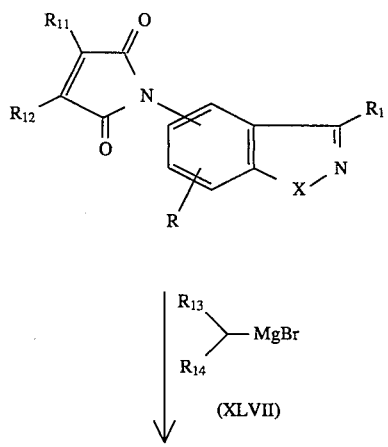

FLOW DIAGRAM XXVI -continued

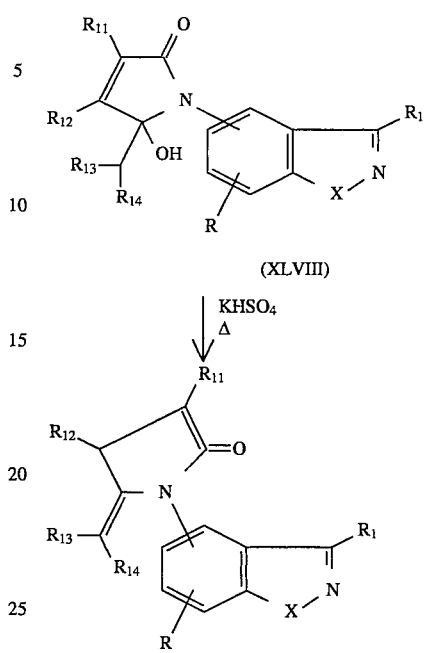

Formula I compounds wherein Q is Q18 may be prepared by reacting an aminobenzisoxazole or aminobenzisothiazole of formula III with an anhydride of formula XLIX in acetic anhydride with a catalytic amount of sodium acetate at an elevated temperature, in acetic acid at an elevated temperature or in xylene with a catalytic amount of p-toluene sulfonic acid at an elevated temperature. The reaction is shown below in Flow Diagram XXVII.

FLOW DIAGRAM XXVII

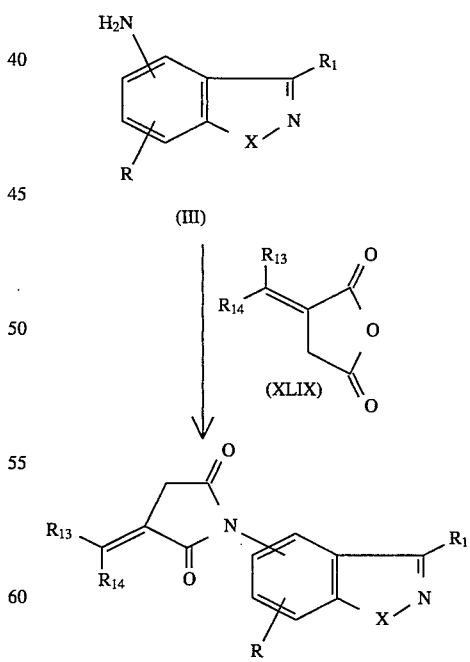

Alternatively, formula I compounds wherein Q is Q18 may be prepared by reacting an aminobenzisoxazole or aminobenzisothiazole of formula III with a diacid of formula L in xylene at reflux. The reaction scheme is shown below in Flow Diagram XXVIII.

FLOW DIAGRAM XXVIII

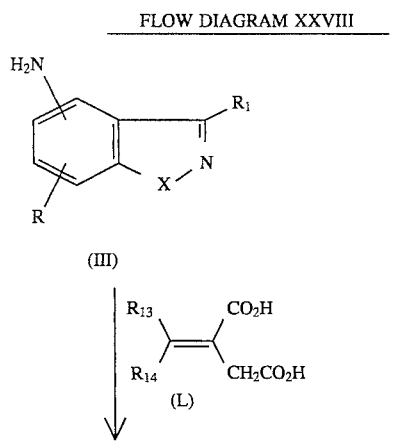

-continued
FLOW DIAGRAM XXVIII

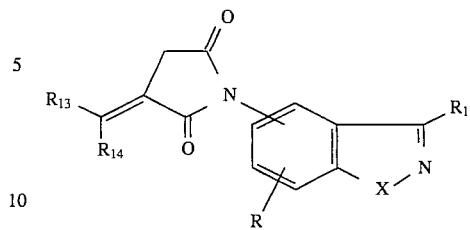

Compounds of formula I wherein Q is Q19 may be prepared by reacting an aminobenzisoxazole or aminobenzisothiazole of formula III with ethyl malonyldiurethane and sodium nitrite in acetic acid with a catalytic amount of concentrated hydrochloric acid to form a hydrazone of formula LI, cyclizing the hydrazone with base to form a triazinedione of formula LII and decarboxylating the triazinedione with mercaptoacetic acid at an elevated temperature and optionally alkylating the formula I compound wherein Q is Q 19 and $R_{11}$ is hydrogen with an alkyl halide and a base such as sodium hydride. The reaction scheme is shown in Flow Diagram

FLOW DIAGRAM XXIX

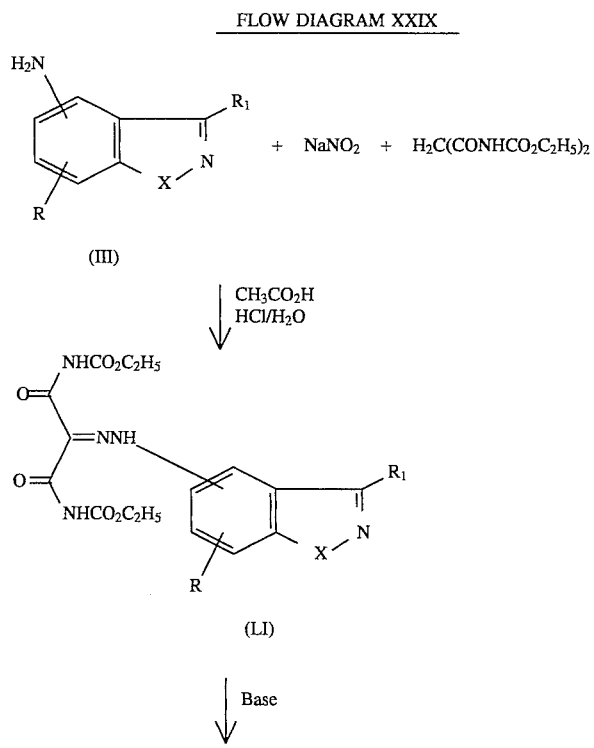

-continued
FLOW DIAGRAM XXIX

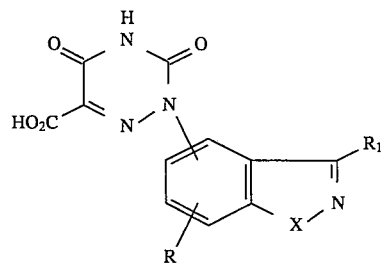

(LII)

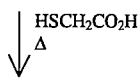

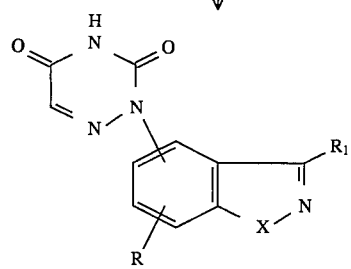

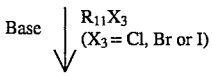

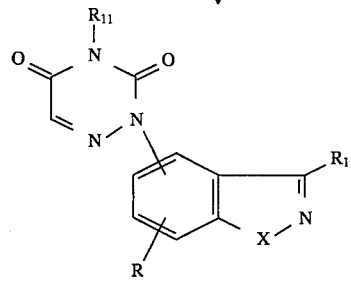

Alternatively, compounds of formula I wherein Q is Q19 and $R_{11}$ is hydrogen may be prepared by reacting a hydrazine of formula XIV with acetone in a sulfuric acid solution to form a hydrazone of formula LIII, reacting the hydrazone with potassium cyanate in an acetic acid solution to form a triazolidine of formula LIV and reacting the triazolidine with pyruvic acid and sulfuric acid. The reaction sequence is shown below in Flow Diagram XXX.

FLOW DIAGRAM XXX

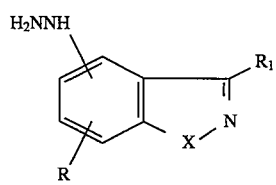

(XIV)

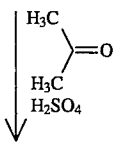

FLOW DIAGRAM XXX -continued

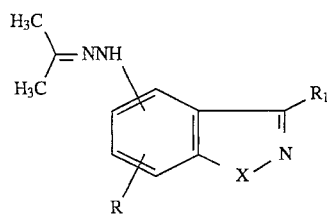

(LIII)

↓ KOCN
CH₃CO₂H/H₂O

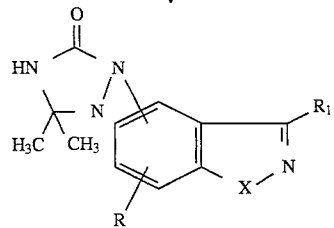

(LIV)

↓ CH₃CCO₂H (O)
  H₂SO₄

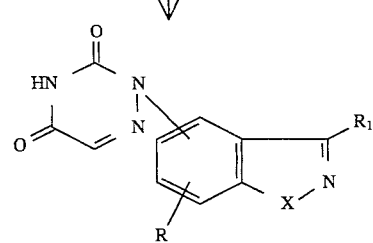

Formula I compounds wherein Q is Q20 may be prepared by reacting an isocyanate of formula IV with an amino ester of formula LV in the presence of a base such as sodium hydride to form an intermediate compound of formula LVI and cyclizing the intermediate compound with acid and optionally alkylating the formula I compound wherein Q is Q20 and $R_{15}$ is hydrogen with a $C_1$–$C_3$alkyl halide and a base such as sodium hydride. The reaction scheme is shown in Flow Diagram XXXI.

FLOW DIAGRAM XXXI

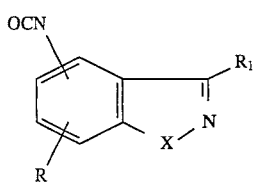

(IV)

↓ $R_{11}$  $CO_2C_2H_5$
  $H_2N$  $R_{12}$
  (LV)

FLOW DIAGRAM XXXI -continued

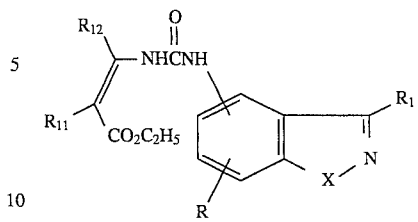

(LVI)

↓ Acid

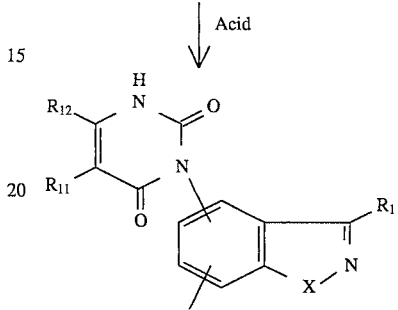

↓ Base | $C_1$–$C_3$alkyl halide

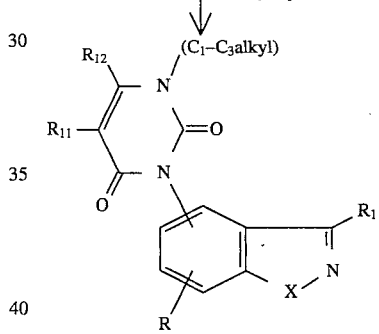

Compounds of formula I wherein Q is Q21 may be prepared by reacting a formula I compound wherein Q is Q20 and $R_{11}$ is hydrogen with sodium borohydride. The reaction is shown below in Flow Diagram XXXII.

FLOW DIAGRAM XXXII

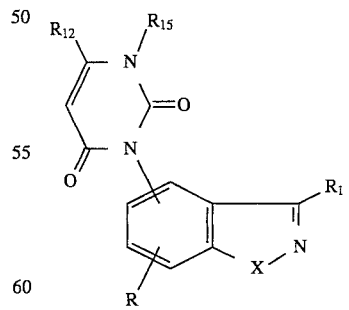

↓ NaBH₄

-continued
FLOW DIAGRAM XXXII

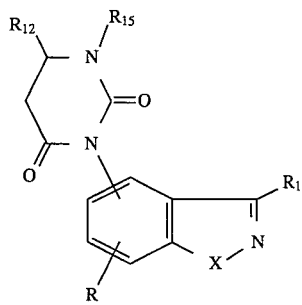

Alternatively, compounds of formula I wherein Q is Q21 may be prepared by reacting an amine of formula LVII with an α,β-unsaturated ester of formula LVIII to form an amino ester of formula LIX and reacting the amino ester with an isocyanate of formula IV followed by heating in an acidic methanol solution. The reaction sequence is shown below in Flow Diagram XXXIII.

FLOW DIAGRAM XXXIII

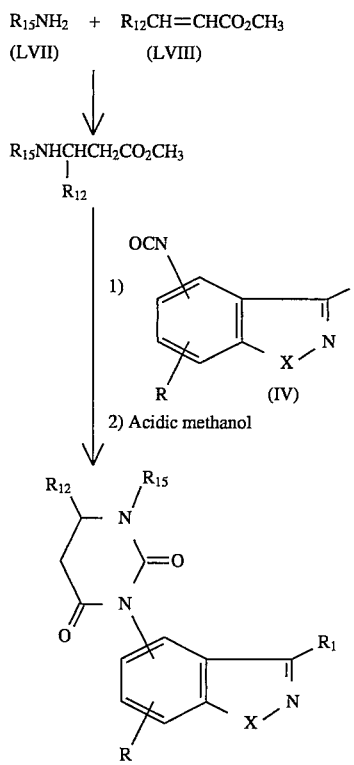

Compounds of formula I wherein Q is Q22 may be prepared by reacting a hydrazine of formula XIV with a β carbonyl aldehyde of formula LX followed by cyclization under acidic conditions to form a dihydropyridazinone of formula LXI and dehydrogenating the dihydropyridazinone with chloranil or 2,3-dichloro-5,6-dicyanobenzoquinone (DDQ) in an inert solvent such as dioxane or toluene at an elevated temperature. The reaction scheme is shown in Flow Diagram XXXIV.

FLOW DIAGRAM XXXIV

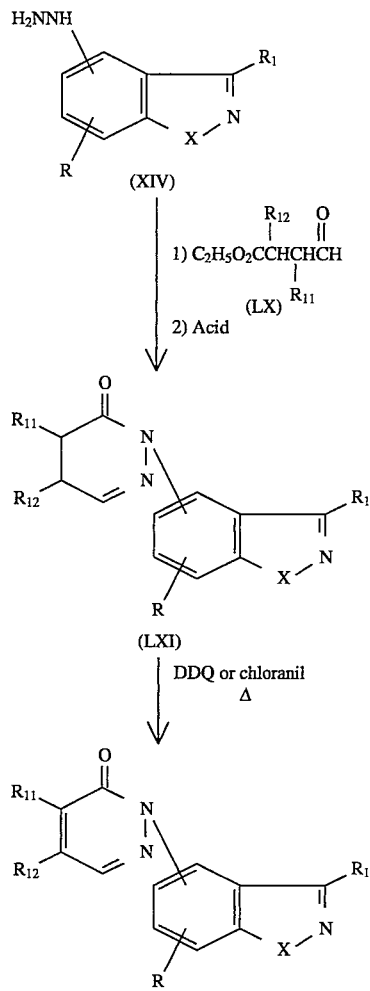

Aminobenzisoxazole and aminobenzisothiazole compounds of formula III may be prepared by reducing a nitrobenzisoxazole or nitrobenzisothiazole of formula LXII with iron in acetic acid. The reaction scheme is shown below in Flow Diagram XXXV.

FLOW DIAGRAM XXXV

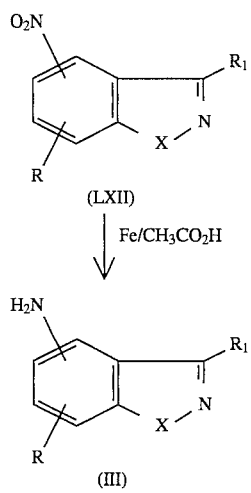

Certain nitrobenzisothiazole compounds of formula LXII may be prepared by reacting a ketone of formula LXIII with ammonia and sulfur. The reaction is shown below in Flow Diagram XXXVI.

FLOW DIAGRAM XXXVI

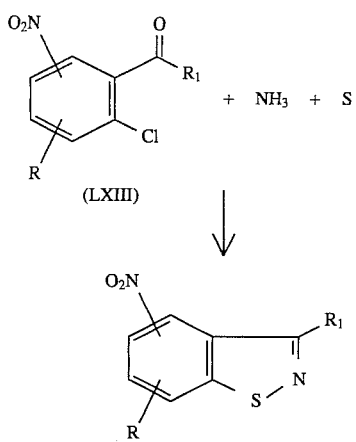

Alternatively, certain nitrobenzisothiazole compounds of formula LXII wherein $R_1$ is $R_2$ and $R_2$ is phenyl optionally substituted as described hereinabove for formula I may be prepared by reacting a benzaldehyde of formula LXIV with a phenyl magnesium bromide of formula LXV to form an alcohol of formula LXVI, oxidizing the alcohol to form a benzophenone of formula LXVII, reacting the benzophenone with a base and methyl mercaptan to form an intermediate compound of formula LXVIII which is converted to its oxime of formula LXIX and reacting the oxime with acetic anhydride and pyridine. The reaction scheme is shown below in Flow Diagram XXXVII.

FLOW DIAGRAM XXXVII

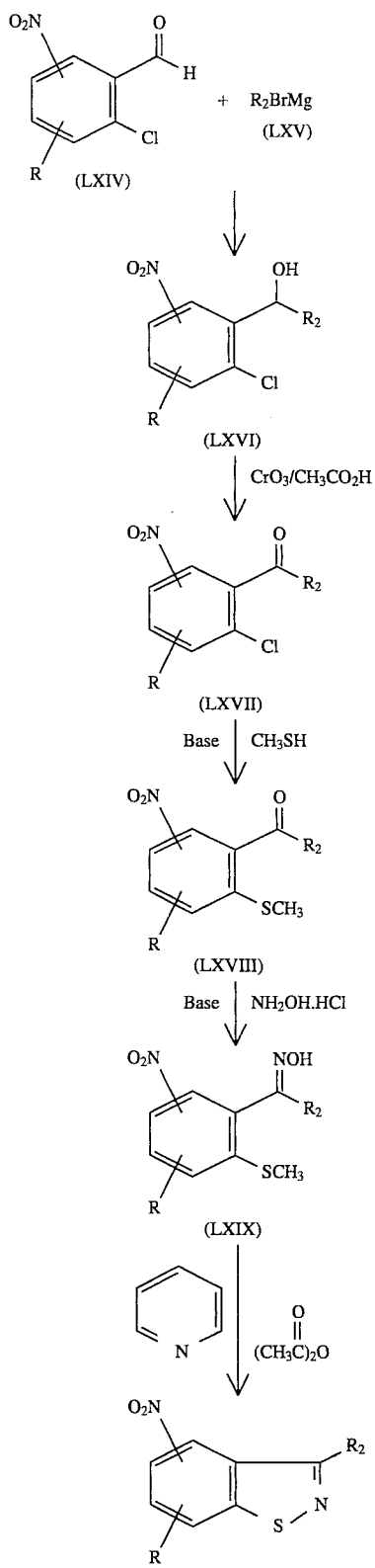

Certain compounds of formula LXVII may also be prepared by reacting a benzoyl chloride of formula LXX with a methoxybenzene of formula LXXI in the presence of a Lewis acid such as aluminum chloride. The reaction is shown below in Flow Diagram XXXVIII.

FLOW DIAGRAM XXXVIII

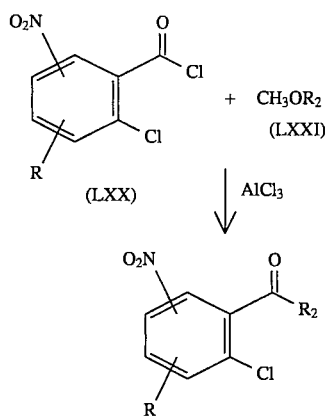

Certain nitrobenzisoxazole compounds of formula LXII wherein $R_1$ is $OR_2$ may be prepared by reacting a methyl salicylate of formula LXXII with hydroxylamine hydrochloride and a base such as sodium methoxide to form a salicylohydroxamic acid of formula LXXIII, reacting the salicylohydroxamic acid with 1,1'-carbonyldiimidazole and a base such as triethylamine to form a 1,2-benzisoxazol- 3-ol of formula LXXIV, reacting the 1,2-benzisoxazol-3-ol with a halide compound of formula LXXV and a base such as potassium carbonate to form an intermediate compound of formula LXXVI and reacting the intermediate compound with nitric acid. The reaction scheme is shown in Flow Diagram XXXIX.

FLOW DIAGRAM XXXIX

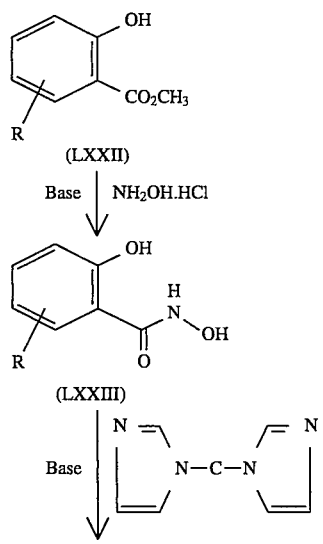

-continued
FLOW DIAGRAM XXXIX

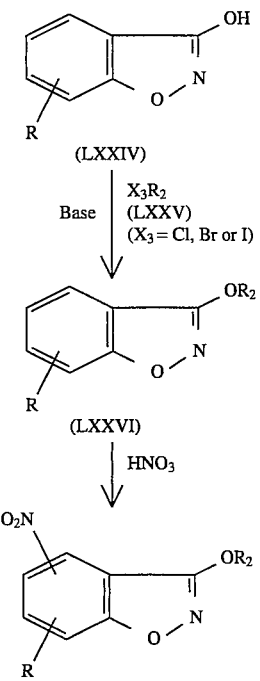

Alternatively, certain nitrobenzisoxazole compounds of formula LXII wherein $R_1$ is $CH_2CO_2(C_1-C_4alkyl)$ may be prepared by reacting a phenol of formula LXXVII with malonic acid and zinc chloride in phosphorus oxychloride to form a 4-hydroxycoumarin of formula LXXVIII, reacting the 4-hydroxycoumarin with hydroxylamine hydrochloride and a base such as sodium methoxide to form a 1,2 -benzisoxazole-3-acetic acid of formula LXXIX, reacting the 1,2-benzisoxazole-3-acetic acid with a $C_1-C_4$alcohol in the presence of hydrogen chloride to form a 1,2-benzisoxazole-3-acetate of formula LXXX and reacting the 1,2-benzisoxazole-3-acetate with nitric acid. The reaction scheme is shown below in Flow Diagram XL.

FLOW DIAGRAM XL

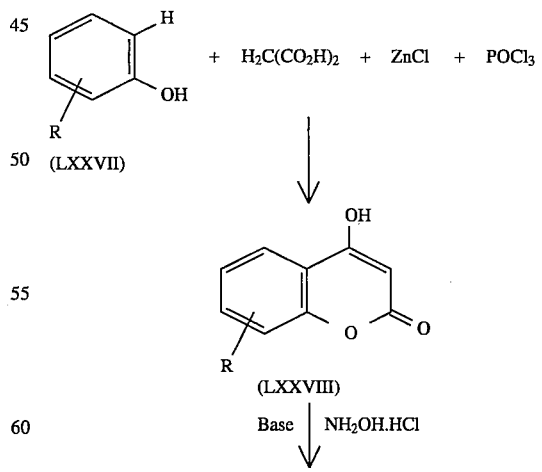

-continued
FLOW DIAGRAM XL

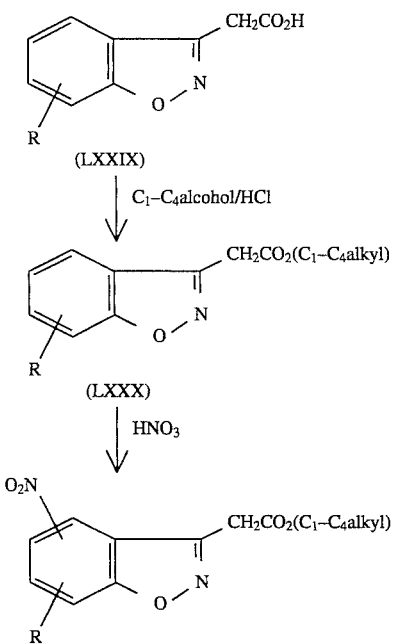

Certain nitrobenzisoxazole compounds wherein $R_1$ is $R_2$ may be prepared by reacting a benzophenone of formula LXVII with hydroxylamine hydrochloride in the presence of a base such as potassium hydroxide to form an oxime of formula LXXXI and reacting the oxime with a base such as potassium hydroxide. The reaction scheme is shown below in Flow Diagram XLI.

FLOW DIAGRAM XLI

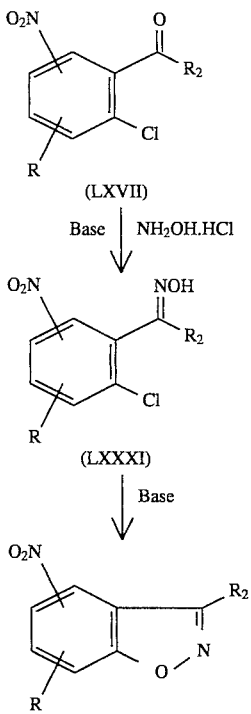

The substituted benzisoxazole and benzisothiazole compounds of the present invention are effective herbicidal agents useful for the control of a wide variety of undesirable plant species. Those compounds are effective for controlling weeds native to both dry land and wet land areas. The compounds are also useful as aquatic herbicides and are effective in controlling the above-said plants when applied to the foliage thereof or to soil or water containing seeds or other propagating organs thereof such as stolons, tubers or rhizomes, at rates of from about 0.016 to 4.0 kg/ha and preferably from about 0.125 to 4.0 kg/ha.

Advantageously, it has been found that the compounds of the present invention are effective for controlling undesirable plant species including important weeds in transplanted rice culture. The compounds may be applied to the soil or water containing transplanted rice plants and seeds or other propagating organs of a variety of weed species.

The compounds of this invention are best suited for use as broad spectrum herbicides, especially when applied postemergence to the locus in which weed control is desired. However, certain compounds of this invention are selective. In fact, some of the compounds of this invention are selective in crops such as soybeans and rice.

While the substituted benzisoxazole and benzisothiazole compounds of this invention are effective for controlling undesirable plant species when employed alone, they may also be used in combination with other biological chemicals, including other herbicides.

The formula I compounds of this invention may be applied to crops in the form of a solid or liquid herbicidal composition, comprising a herbicidally effective amount of the formula I compound dispersed or dissolved in an agronomically acceptable, inert solid or liquid carrier. The compositions may be applied as preemergence or postemergence treatments.

The formula I compounds may be formulated as emulsifiable concentrates, wettable powders, granular formulations, flowable concentrates and the like.

In order to facilitate a further understanding of the invention, the following examples are presented primarily for the purpose of illustrating more specific details thereof. The invention should not be deemed limited by the examples as the full scope of the invention is defined in the claims. The term NMR designates nuclear magnetic resonance spectroscopy.

EXAMPLE 1

Preparation of Methyl 4-chlorosalicylate

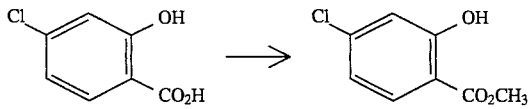

Hydrogen chloride gas is bubbled into a mixture of 4-chlorosalicylic acid (100 g, 0.579 mol) in methanol while maintaining the temperature at 45°–50° C. The reaction mixture is then stirred at room temperature for several hours, concentrated in vacuo and extracted with ether. The combined organic extracts are washed sequentially with brine, saturated sodium hydrogen carbonate solution and brine, dried over anhydrous sodium sulfate and concentrated in vacuo to obtain an amber oil. The oil is distilled under reduced pressure to give the title product as a colorless oil which is identified by NMR spectral analyses.

EXAMPLE 2

Preparation of 4-Chlorosalicylohydroxamic acid

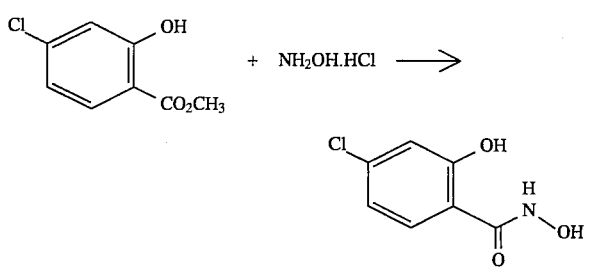

Hydroxylamine hydrochloride (20.65 g, 0.297 mol) is added to a mixture of sodium methoxide (53 g, 0.99 mol) in methanol while maintaining the temperature below 10° C. A mixture of methyl 4-chlorosalicylate (46.2 g, 0.248 mol) in methanol is then added to the reaction mixture and the resultant mixture is stirred at room temperature for 10 days, acidified with concentrated hydrochloric acid (pH3) and filtered to give the title product as an off-white solid which is identified by NMR spectral analyses.

Using essentially the same procedure, but substituting phenyl 4-fluorosalicylate for methyl 4-chlorosalicylate, 4-fluorosalicylohydroxamic acid is obtained as a peach-white solid, mp 184° C. (dec.).

EXAMPLE 3

Preparation of 6-Chloro-1,2-benzisoxazol-3-ol

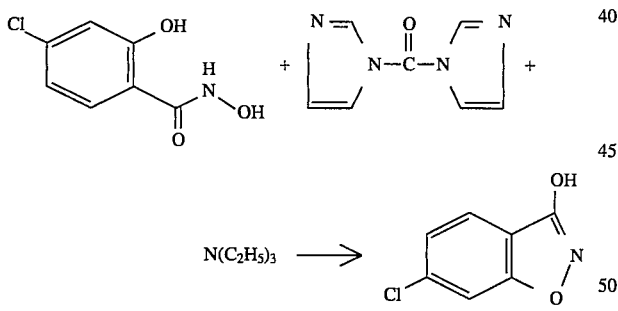

A solution of 1,1'-carbonyldiimidazole (12.76 g, 78.5 mmol) and triethylamine (12.6 mL, 90 mmol) in tetrahydrofuran is slowly added to a refluxing suspension of 4-chlorosalicylohydroxamic acid (13.39 g, 71.4 mmol) in tetrahydrofuran. The reaction mixture is refluxed for 1 hour, cooled, concentrated in vacuo, diluted with water, acidified with concentrated hydrochloric acid (pH1) and filtered to obtain a solid. A solution of the solid in ether is extracted with saturated sodium hydrogen carbonate solution. The combined aqueous extracts are acidified with concentrated hydrochloric acid and the resultant precipitate is collected and dried overnight to give the title product as a white solid, mp 218°–219° C.

Using essentially the same procedure, the following compounds are obtained:

| $R_2$ | mp °C. |
|---|---|
| F | 169–171 |
| H | 140–143 |

EXAMPLE 4

Preparation of Methyl 2-[(6-chloro-1,2-benzisoxazol- 3-yl)oxy]propionate

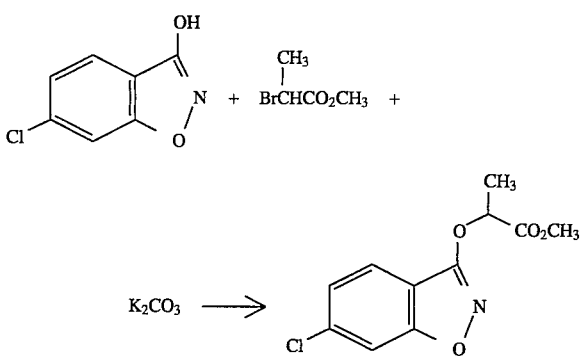

A mixture of 6-chloro-1,2-benzisoxazol-3-ol (6.8 g, 40.1 mmol), potassium carbonate (8.3 g, 60 mmol) and methyl 2-bromopropionate (10.0 g, 60.1 mmol) in N,N-dimethylformamide is stirred at room temperature over-night and diluted with water. The resultant aqueous mixture is acidified with concentrated hydrochloric acid (pH5–pH6) and extracted with methylene chloride. The combined organic extracts are diluted with hexanes, washed with water, dried over anhydrous sodium sulfate and concentrated in vacuo to obtain a residue. Column chromatography of the residue using silica gel and ethyl acetate/hexanes solutions gives the title product as a gold oil which is identified by NMR spectral analyses.

Using essentially the same procedure, the following compounds are obtained:

| R | $R_1$ | mp °C. |
|---|---|---|
| F | $CH_2CO_2CH_3$ | 82–84 |
| H | $CHCO_2CH_3$<br>\|<br>$CH_3$ | |

EXAMPLE 5

Preparation of Methyl 2-[(6-chloro-5-nitro-1,2-benzisoxazol-3-yl)oxy]propionate

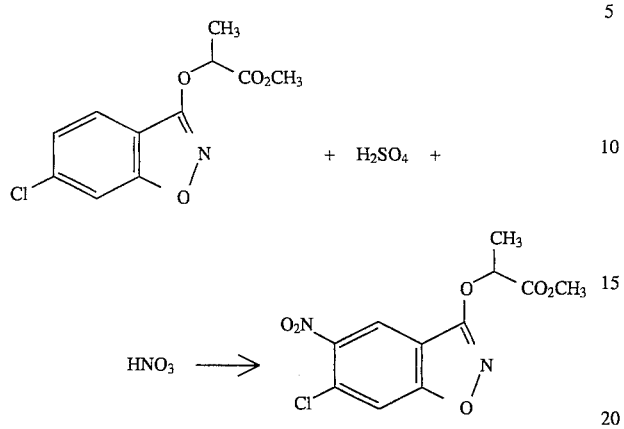

Nitric acid (70%, 3.0 mL, 47 mmol) is slowly added to a mixture of methyl 2-[(6-chloro-1,2-benzisoxazol-3-yl)oxy] propionate (6.0 g, 23.5 mmol) in concentrated sulfuric acid (50 mL) while maintaining the temperature below 10° C. The reaction mixture is stirred for 1 hour on an ice/water bath and poured onto ice. The resultant aqueous mixture is diluted with ether, stirred for several minutes and the ether is allowed to evaporate overnight. The resultant mixture is filtered to obtain a solid which is dissolved in methylene chloride. The methylene chloride solution is dried over anhydrous sodium sulfate and concentrated in vacuo to obtain a solid which is recrystallized from an ether/hexanes solution to give the title product as a solid, mp 98°–101° C.

Using essentially the same procedure, the following compounds are obtained:

| R | $R_1$ | mp °C. |
|---|---|---|
| F | OCHCO$_2$CH$_3$<br>\|<br>CH$_3$ | |
| H | OCHCO$_2$CH$_3$<br>\|<br>CH$_3$ | 103–105 |
| H | OH | 200–202 |

EXAMPLE 6

Preparation of Methyl 2-[(5-amino-6-chloro-1,2-benzisoxazol-3-yl)oxy]propionate, hydrochloride salt

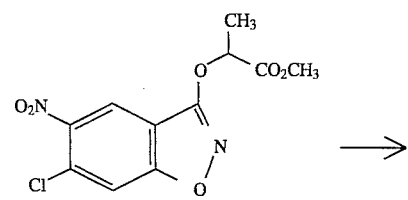

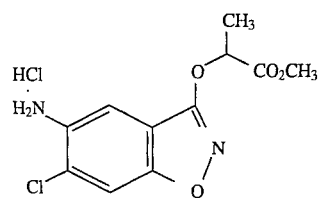

A suspension of methyl 2-[(6-chloro-5-nitro-1,2-benzisoxazol-3-yl)oxy]propionate (2.0 g, 6.7 mmol), 5% palladium on activated carbon (0.1 g) and concentrated hydrochloric acid (0.6 mL) in ethanol is hydrogenated until 430 mL of hydrogen is taken up. The reaction mixture is then filtered through diatomaceous earth and concentrated in vacuo to give the title product as a brown gum which is identified by NMR spectral analyses.

Using essentially the same procedure, the following compounds are obtained:

| R | $R_1$ |
|---|---|
| H | OH |
| F | CH$_2$CO$_2$CH$_3$ |
| F | OCH$_2$CO$_2$CH$_3$ |
| H | ![phenol-OH] |
| H | CH$_2$CO$_2$CH$_3$ |
| H | OCHCO$_2$CH$_3$<br>\|<br>CH$_3$ |
| F | CHCO$_2$CH$_3$<br>\|<br>CH$_3$ |

EXAMPLE 7

Preparation of Methyl 2-{[6-chloro-5-(1-cyclohexene-1,2-dicarboximido)-1,2-benzisoxazol-3-yl]oxy}propionate

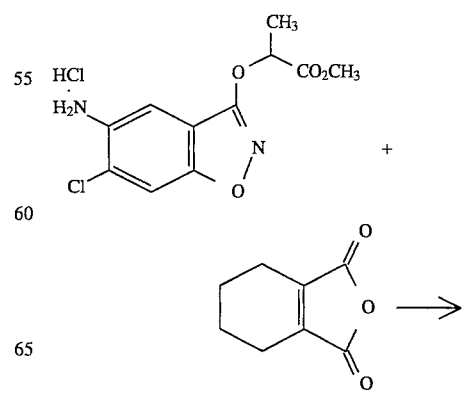

-continued

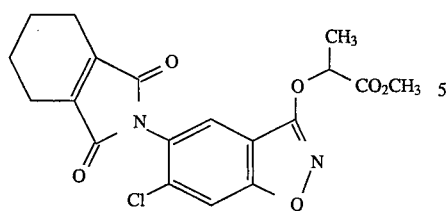

A mixture of methyl 2-[(5-amino-6-chloro-1,2-benzisoxazol-3-yl)oxy]propionate, hydrochloride salt (3.0 g, 6.6 mmol), 3,4,5,6-tetrahydrophthalic anhydride (1.22 g, 8.03 mmol) and sodium acetate (0.66 g, 8.05 mmol) in acetic acid is refluxed for one hour, concentrated in vacuo, diluted with sodium hydrogen carbonate solution and extracted with ether. The organic extracts are combined, washed sequentially with saturated sodium hydrogen carbonate solution and brine, dried over anhydrous sodium sulfate and concentrated in vacuo to obtain a brown gum. Column chromatography of the gum using silica gel and ether/hexanes solutions gives the title product as a white solid which is identified by $^1$HNMR spectral analysis.

Using essentially the same procedure, the following compounds are obtained:

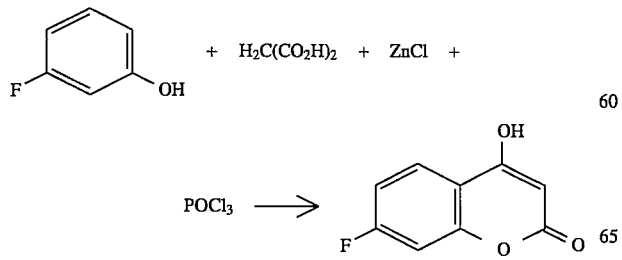

| R | $R_1$ | mp °C. |
|---|---|---|
| F | $CH_2CO_2CH_3$ | 108–111 |
| F | $OCH_2CO_2CH_3$ | 124–127 |
| H | ![phenol-CH3] | |
| H | $OCHCO_2CH_3$<br>\|<br>$CH_3$ | 96–102 |
| H | $CH_2CO_2CH_3$ | 116–119 |
| H | OH | 253–255 |

EXAMPLE 8

Preparation of 7-Fluoro-4-hydroxycoumarin

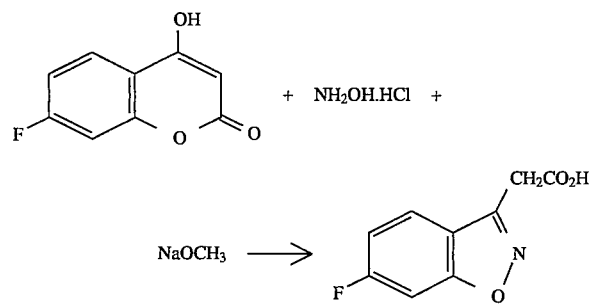

A mixture of 3-fluorophenol (31.5 g, 0.281 mol), malonic acid (29.24 g, 0.281 g) and zinc chloride (100.0 g, 0.734 mol) in phosphorus oxychloride (70 mL, 0.751 mol) is heated at 65° C. overnight and poured into an ice/water mixture. The resultant aqueous mixture is filtered to obtain a pale green solid. A mixture of the solid in 10% sodium hydrogen carbonate solution is stirred at room temperature for 2 hours, decolorized with charcoal and filtered through diatomaceous earth. The filtrate is acidified with concentrated hydrochloric acid and the resultant precipitate is collected and dried to give the title product as a brown solid, mp 229°–230° C.

EXAMPLE 9

Preparation of 6-Fluoro-1,2-benzisoxazole-3-acetic acid

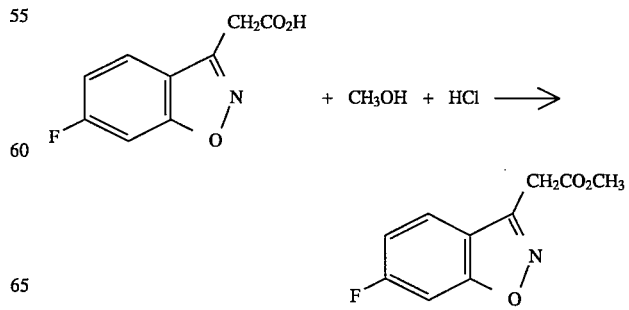

A solution of sodium methoxide (22.3 g, 0.412 mol) in methanol is added to a solution of hydroxylamine hydrochloride (30.4 g, 0.438 mol) in methanol. The resultant mixture is stirred at room temperature for 30 minutes and filtered. The filtrate is added to a refluxing solution of 7-fluoro-4-hydroxycoumarin (18.5 g, 0.103 mol) in methanol. The reaction mixture is refluxed overnight and concentrated in vacuo to obtain a yellow solid. A solution of the solid in a sodium hydrogen carbonate solution is washed with ether and acidified with 6N hydrochloric acid. The resultant precipitate is filtered and dried to give a solid which is recrystallized from water to give the title product as a beige solid, mp 132°–133° C.

Using essentially the same procedure, but substituting 4-hydroxycoumarin for 7-fluoro-4-hydroxycoumarin, 1,2-benzisoxazole-3-acetic acid is obtained as an off-white solid, mp 123°–127° C.

EXAMPLE 10

Preparation of Methyl 6-fluoro-1,2-benzisoxazole-3-acetate

Hydrogen chloride gas is bubbled into a cold (ice/water bath) solution of 6-fluoro-1,2-benzisoxazole- 3-acetic acid (13.7 g, 0.0702 mol) in methanol over a 15 minute period. The reaction mixture is concentrated in vacuo to obtain a brown-orange solid. Flash column chromatography of the solid using silica gel and methylene chloride gives the title product as a white solid, mp 60°–61° C.

Using essentially the same procedure, but substituting 1,2-benzisoxazole-3-acetic acid for 6-fluoro-1,2 -benzisoxazole-3-acetic acid, methyl 1,2-benzisoxazole-3-acetate is obtained as an oil.

EXAMPLE 11

Preparation of Methyl 6-fluoro-5-nitro-1,2-benzisoxazole-3-acetate

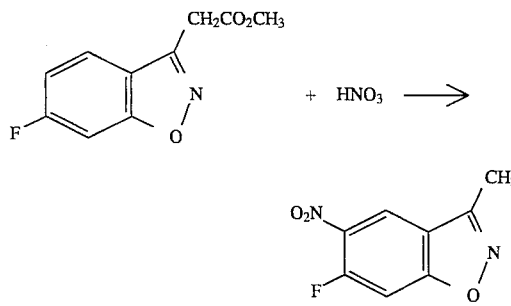

Methyl 6-fluoro-1,2-benzisoxazole-3-acetate (6.0 g, 28.7 mmol) is added portionwise to nitric acid (90%, 60 mL) at 0° C. The reaction mixture is stirred at 0° C. for 30 minutes and poured into an ice/water mixture. The aqueous mixture is extracted with methylene chloride. The organic extracts are combined, washed sequentially with water, saturated sodium hydrogen carbonate solution and brine, dried over anhydrous magnesium sulfate and concentrated in vacuo to obtain a yellow oil. Flash column chromatography of the oil using silica gel and ether/petroleum ether solutions gives the title product as a pale yellow solid which is identified by $^1$HNMR spectral analysis.

Using essentially the same procedure, the following compounds are obtained:

| R | $R_1$ | mp °C. |
|---|---|---|
| F | $OCH_2CO_2CH_3$ | 104–106 |
| F | $CH_2CO_2CH_3$ | 65–67 |
| F | CHCO$_2$CH$_3$<br>\|<br>CH$_3$ | 124.5–126 |

EXAMPLE 12

Preparation of Methyl 5-(3,4-dimethyl-2,5-dioxo-3-pyrrolin-1-yl)-6-fluoro-α-methyl-1,2-benzisoxazole-3-acetate

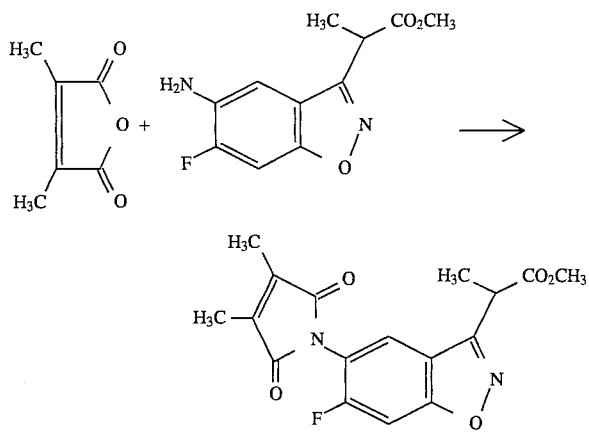

A solution of methyl 5-amino-6-fluoro-α-methyl-1,2-benzisoxazole-3-acetate (2.6 g, 11.0 mmol) in acetic acid is added to 2,3-dimethylmaleic anhydride (1.39 g, 11.0 mmol). The reaction mixture is refluxed for several hours and concentrated in vacuo to obtain a brown oil. A solution of the oil in ether is washed sequentially with sodium hydrogen carbonate solution and brine, dried over anhydrous sodium sulfate and concentrated in vacuo to obtain a brown oil. Column chromatography of the oil using silica gel and ether/hexanes solutions gives the title product as a white solid, mp 106°–107° C.

Using essentially the same procedure, but substituting 3,4,5,6-tetrahydrophthalic anhydride for 2,3-dimethylmaleic anhydride, methyl 5-(1-cyclohexene-1,2 -dicarboximido)-6-fluoro-α-methyl-1,2-benzisoxazole-3-acetate is obtained as a white solid, mp 117° C.

EXAMPLE 13

Preparation of Methyl 6-fluoro-α-methyl-1,2-benzisoxazole-3-acetate

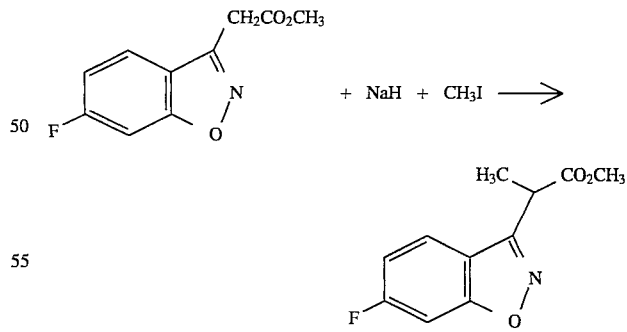

Sodium hydride (2.32 g, 57.9 mmol, 60% in oil) is added portionwise to a solution of methyl 6-fluoro-1,2-benzisoxazole-3-acetate (12.07 g, 57.7 mmol) in tetrahydrofuran at −2° C. The mixture is stirred for 30 minutes at 2° C., treated with methyl iodide (10.65 g, 75.0 mmol), stirred at 5° C. for 50 minutes and poured onto ice. The aqueous mixture is extracted with methylene chloride. The organic extracts are combined, dried over anhydrous sodium sulfate and concentrated in vacuo to give the title product as an oil which is identified by NMR spectral analyses.

EXAMPLE 14

Preparation of N-[3-(Allyloxy)-1,2-benzisoxazol-5-yl]-1-cyclohexene-1,2-dicarboximide

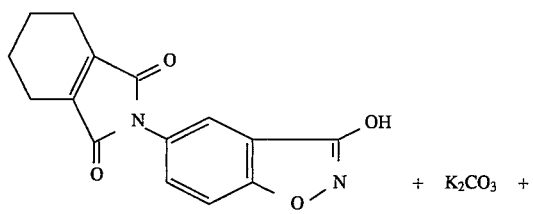

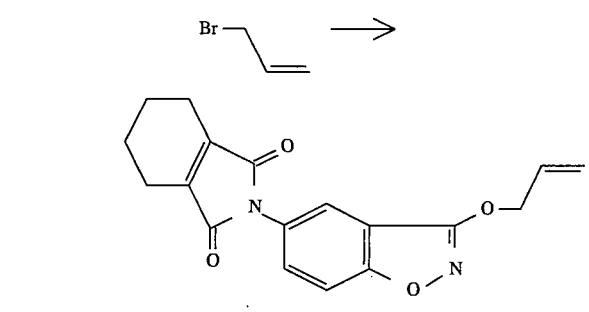

A mixture of N-(3-hydroxy-1,2-benzisoxazol-5-yl)-1-cyclohexene-1,2-dicarboximide (0.75 g, 2.64 mmol), potassium carbonate (0.6 g, 4.35 mmol) and allyl bromide (1 g, 8.3 mmol) in N,N-dimethylformamide is heated at 60°–70° C. for 2 hours and diluted with water. The aqueous mixture is extracted with ether. The organic extracts are combined, washed sequentially with water and brine, dried over anhydrous sodium sulfate and concentrated in vacuo to obtain a yellow oil. Column chromatography of the oil using silica gel and ether/hexanes solutions yields a gum. A solution of the gum in an ether/hexanes mixture is passed through a plug of silica gel and crystallized to give the title product as a pale yellow solid, mp 88°–89° C.

Using essentially the same procedure, but substituting propargyl bromide for allyl bromide, N-[3-(2-propynyloxy)-1,2-benzisoxazol-5-yl]-1-cyclohexene-1,2-dicarboximide is obtained as a pale yellow solid, mp 147°–148° C.

EXAMPLE 15

Preparation of 2-Chloro-2'-methoxy-5-nitrobenzhydrol

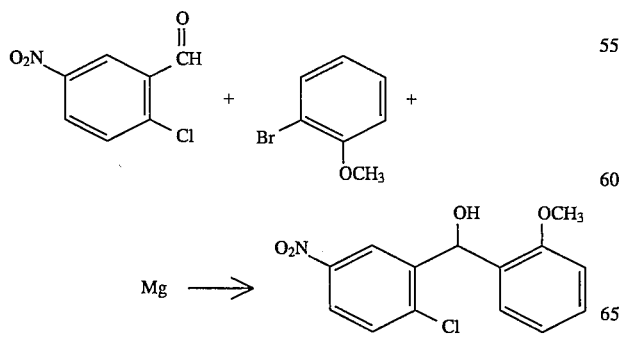

A solution of 2-bromoanisole (50 g, 0.267 mol) in ether is added portionwise to a mixture of magnesium (7.1 g, 0.293 mol) in ether. After the addition is complete, the reaction mixture is heated at reflux for 1 hour, diluted with ether, cooled to 0° C., treated with a solution of 2-chloro-5-nitrobenzaldehyde (39 g, 0.210 mol) in tetrahydrofuran, warmed to room temperature and diluted with an ice/water mixture. After acidifying the aqueous mixture with hydrochloric acid (pH2–pH3), the organic phase is separated and the aqueous phase is extracted with ether. The extracts are combined, washed sequentially with 10% sodium hydrogen carbonate solution and brine, dried over anhydrous sodium sulfate and concentrated in vacuo to give the title product as a brown gum.

EXAMPLE 16

Preparation of 2-Chloro-2'-methoxy-5-nitrobenzophenone

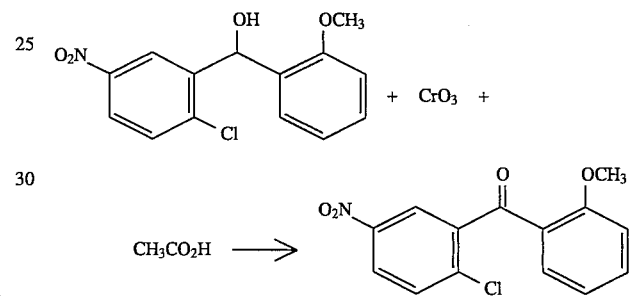

A solution of chromium(VI) oxide (91 g, 0.919 mol) in a 1:4 water/acetic acid solution is added portionwise to 2-chloro-2'-methoxy-5-nitrobenzhydrol (64.2 g, 0.219 mol) while maintaining the reaction mixture temperature at 25°–35° C. The reaction mixture is then stirred at 25°–35° C. for 1 hour, cooled, diluted with water and concentrated in vacuo to obtain a residue. The residue is diluted with water and extracted with methylene chloride. The organic extracts are combined, dried over anhydrous sodium sulfate, mixed with silica gel (10 g) and filtered. The filtrate is concentrated in vacuo to obtain an oil. A solution of the oil in a methanol/water solution is decolorized with charcoal and concentrated in vacuo to yield a residue. Column chromatography of the residue using silica gel and methylene chloride/hexanes solutions gives the title product as a white solid.

EXAMPLE 17

Preparation of the Oxime of 2-chloro-2'-methoxy-5-nitrobenzophenone

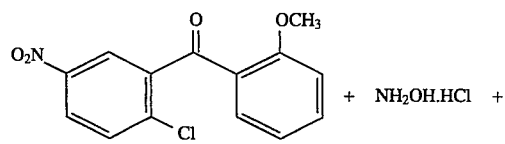

-continued

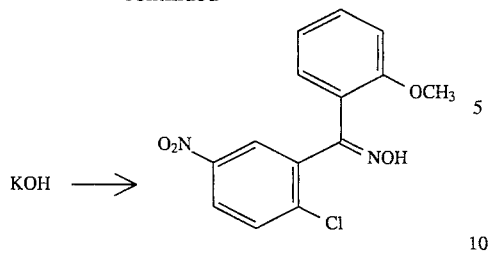

2-Chloro-2'-methoxy-5-nitrobenzophenone (1.44 g, 4.94 mmol) is added to a mixture of sodium acetate (0.61 g, 7.48 mmol) and hydroxylamine hydrochloride (0.52 g, 7.48 mmol) in a 1:10 water/ethanol mixture. The reaction mixture is refluxed for 6 hours, cooled, diluted with water and filtered. The filtrate is extracted several times with methylene chloride. The extracts are combined, washed with water, dried over anhydrous sodium sulfate and filtered. The filtrate is diluted with hexanes to the cloud point, treated with silica gel (1 g) and filtered. The filtrate crystallizes and the solid is collected to give the title product as a solid, mp 173°–178° C.

EXAMPLE 18

Preparation of 3-(o-Methoxyphenyl)-5-nitro-1,2-benzisoxazole

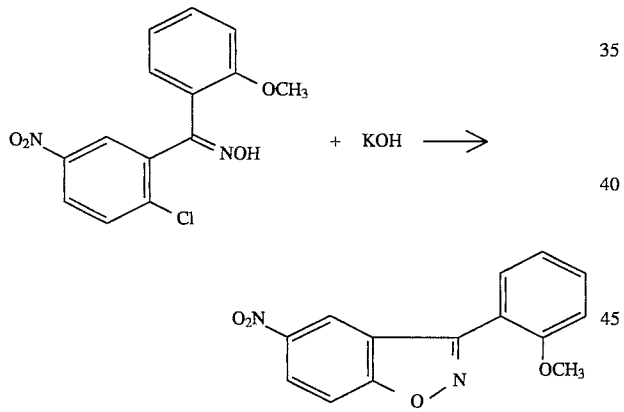

A solution of the oxime of 2-chloro-2'-methoxy-5-nitrobenzophenone (6.5 g, 16.28 mmol) in a 2:1 ethanol/tetrahydrofuran mixture is added portionwise to a solution of potassium hydroxide in ethanol. The reaction mixture is stirred for 45 minutes, treated with additional potassium hydroxide (4.9 g), stirred for several minutes, diluted with ice-water, acidified with concentrated hydrochloric acid (pH1–pH2) and extracted with methylene chloride. The organic extracts are combined, washed sequentially with brine and saturated sodium hydrogen carbonate solution, dried over anhydrous sodium sulfate, diluted with hexanes, allowed to crystallize. The title product is collected by filtration, and the filtrate is concentrated in vacuo to give a solid. Column chromatography of the solid using silica gel and methylene chloride/hexanes solutions gives additional title product as a white solid, mp 170°–171° C.

EXAMPLE 19

Preparation of o-(5-Nitro-1,2-benzisoxazol-3-yl)phenol

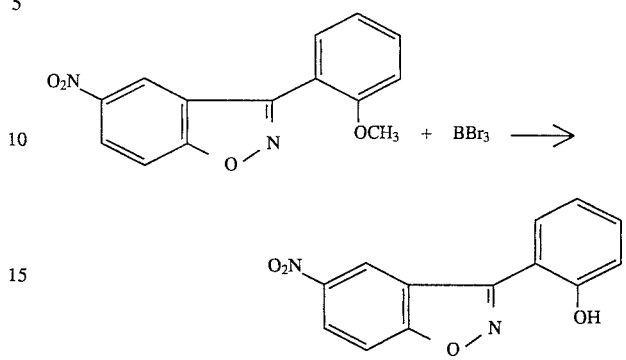

A 1 molar solution of boron tribromide in methylene chloride (15 mL, 15 mmol) is added to a solution of 3-(o-methoxyphenyl)-5-nitro-1,2-benzisoxazole (1.96 g, 7.25 mmol) in methylene chloride at 0° C. The reaction mixture is warmed to and stirred at room temperature for 2 hours and diluted with an ice/water mixture. The phases are separated and the aqueous phase is extracted with methylene chloride. The organic phase and methylene chloride extracts are combined, dried over anhydrous sodium sulfate and concentrated in vacuo to give the title product as a solid, mp 172°–176° C.

EXAMPLE 20

Preparation of Methyl {o-[5-(1-cyclohexene-1,2-dicarboximido)-1,2-benzisoxazol-3-yl]phenoxy}acetate

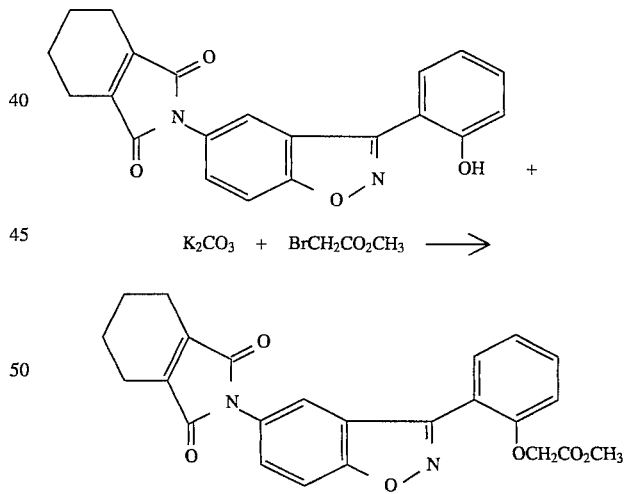

Methyl bromoacetate (0.75 mL, 7.69 mmol) is added to a mixture of N-[3-(o-hydroxyphenyl)-1,2-benzisoxazol-5-yl]-1-cyclohexene-1,2-dicarboximide (1.0 g, 2.77 mmol) and potassium carbonate (0.61 g, 4.42 mmol) in N,N-dimethylformamide. The reaction mixture is stirred overnight at room temperature, diluted with an ice/water mixture and extracted with methylene chloride. The organic extracts are combined, washed with water, dried over anhydrous sodium sulfate and concentrated in vacuo to obtain a dark oil. Column chromatography of the oil using silica gel and ether/hexanes solutions gives a pale yellow solid. The solid is dissolved in a methylene chloride/hexanes mixture, treated with silica gel, filtered and crystallized on an ice bath. The solid is collected and dried to give the title product as a pale yellow solid, mp 119°–122° C.

Using essentially the same procedure, but substituting methyl 2-bromopropionate for methyl bromoacetate, methyl {o-[5-(1-cyclohexene-1,2-dicarboximido)-1,2-benzisoxazol-3-yl]phenoxy}-α-methylacetate is obtained as a pale yellow gum.

EXAMPLE 21

Preparation of Methyl 5-amino-1,2-benzisothiazole-3-acetate

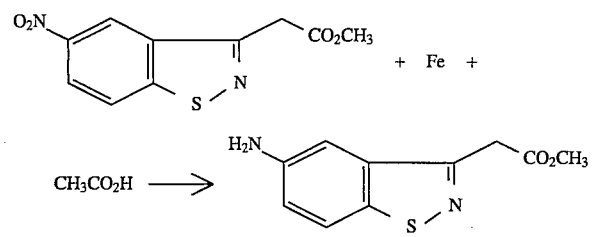

Iron (0.74 g, 13.3 mmol) is added portionwise to a solution of methyl 5-nitro-1,2-benzisothiazole-3-acetate (0.67 g, 2.7 mmol) in acetic acid at 50° C. The reaction mixture is stirred at 50° C. for several minutes, cooled and filtered through diatomaceous earth. The resultant filtrate, which contains the title product, is used in Example 22 without further purification.

Using essentially the same procedure, the following compounds are obtained:

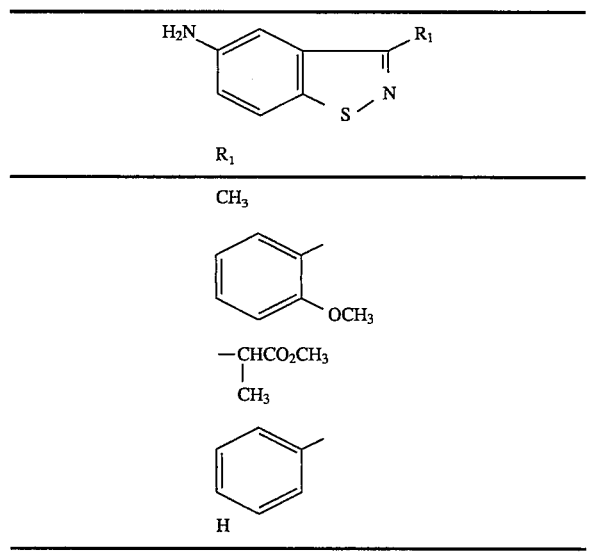

EXAMPLE 22

Preparation of Methyl 5-(1-cyclohexene-1,2-dicarboximido)-1,2-benzisothiazole-3-acetate

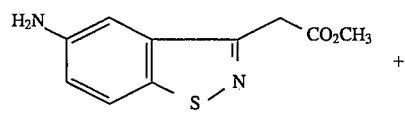

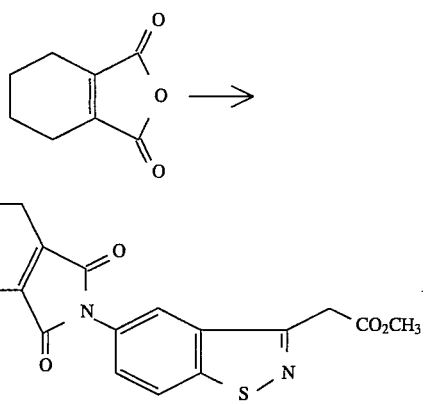

A mixture of the filtrate obtained in Example 21 and 3,4,5,6-tetrahydrophthalic anhydride (0.44 g, 2.65 mmol) is heated at reflux for several minutes, cooled and filtered through diatomaceous earth. The resultant filtrate is concentrated in vacuo to obtain a residue. A solution of the residue in methylene chloride is washed with sodium hydrogen carbonate solution, dried over anhydrous sodium sulfate and concentrated in vacuo to give a gum. Chromatography of the gum using silica gel and ether/hexanes solutions yields a solid which is recrystallized from a methylene chloride/hexanes solution to give the title product as an orange solid (0.38 g, mp 143°–144° C.).

Using essentially the same procedure, but using the appropriately substituted 5-amino-1,2-benzisothiazole and the appropriate anhydride, the following compounds are obtained:

| $R_{11}$ | $R_{12}$ | $R_1$ | mp °C. |
|---|---|---|---|
| —$CH_2CH_2CH_2CH_2$— | | (o-OCH₃ phenyl) | 177–178 |
| —$CH_2CH_2CH_2CH_2$— | $CH_3$ | | 148–150 |
| —$CH_2CH_2CH_2CH_2$— | | —CHCO₂CH₃ / CH₃ | 129–130 |
| —$CH_2CH_2CH_2CH_2$— | | (phenyl) | 129–130 |
| $CH_3$ | $CH_3$ | (phenyl) | 173–174.5 |
| $CH_3$ | $CH_3$ | H | 201–202 |
| —$CH_2CH_2CH_2CH_2$— | | H | 204.5–205.5 |

EXAMPLE 23

Preparation of Methyl α-methyl-1,2-benzisothiazole-3-acetate

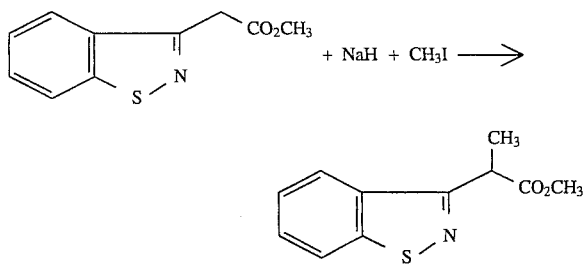

A mixture of sodium hydride (1.25 g, 60% in oil, 31.3 mmol) in tetrahydrofuran is added to a solution of methyl 1,2-benzisothiazole-3-acetate (6.0 g, 29.0 mmol) in tetrahydrofuran. After stirring for 30 minutes, the reaction mixture is treated with methyl iodide (2.0 mL, 32.0 mmol), stirred for one hour and quenched with ice. The aqueous mixture is neutralized with hydrochloric acid (pH5–pH6) and extracted with methylene chloride. The organic extracts are combined, dried over anhydrous sodium sulfate and concentrated in vacuo to obtain a brown oil. Chromatography of the oil using silica gel and 10% to 25% ether in hexanes solutions gives the title product as an amber oil which is identified by NMR spectral analyses.

EXAMPLE 24

Preparation of Methyl α-methyl-5-nitro-1,2-benzisothiazole-3-acetate

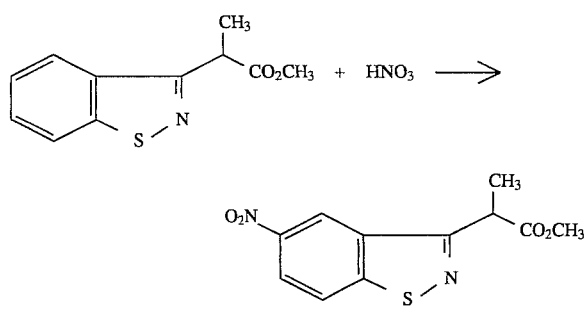

Methyl α-methyl-1,2-benzisothiazole-3-acetate (15.96 g, 72.13 mmol) is added dropwise to nitric acid (90%, 100 mL) while maintaining the reaction mixture temperature below 5° C. The reaction mixture is stirred overnight, poured onto ice and extracted with methylene chloride. The organic extracts are combined, washed sequentially with water, saturated sodium hydrogen carbonate solution and brine, dried over anhydrous sodium sulfate and concentrated in vacuo to obtain an orange oil. Column chromatography of the oil using silica gel and ether/hexanes solutions gives the title product as an orange solid, mp 88°–90° C.

EXAMPLE 25

Preparation of 3-Methyl-5-nitro-1,2-benzisothiazole

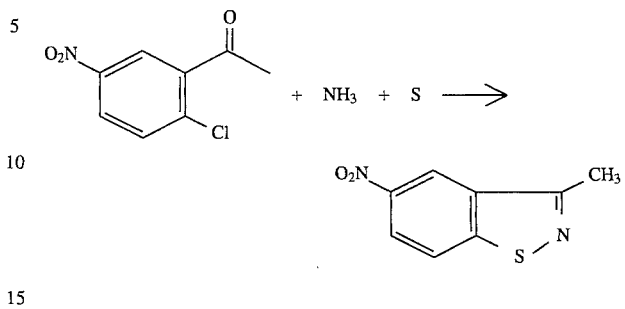

Anhydrous ammonia (30 g) is added to methanol in a steel bomb cooled in an ice/water bath. After the addition is complete, 2-chloro-5-nitroacetophenone (12.1 g, 60.7 mmol) and sulfur (2.0 g, 62.4 mmol) are added to the reaction mixture. The bomb is sealed, heated at about 80°–85° C. overnight, cooled in an ice/water bath and vented. The reaction mixture is diluted with methanol and concentrated in vacuo to obtain a yellow solid. A solution of the yellow solid in methylene chloride is passed through a dry silica gel pad and concentrated in vacuo to yield a solid which is recrystallized from a methylene chloride/hexanes solution to give the title product as a solid, mp 124°–125° C.

EXAMPLE 26

Preparation of 2'-Methoxy-2-(methylthio)-5-nitrobenzophenone

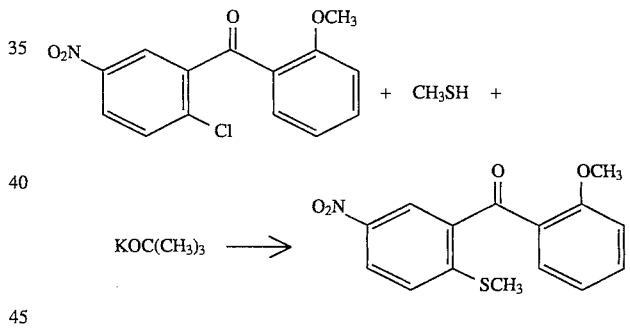

A solution of methanethiol (1.7 g, 35.3 mmol) in tetrahydrofuran is added to a solution of potassium tertbutoxide (4.0 g, 35.7 mmol) in tetrahydrofuran at 0° C. A solution of 2-chloro-2'-methoxy-5-nitrobenzophenone (10.0 g, 34.3 mmol) is added portionwise to the cold reaction mixture. The reaction mixture is then warmed to and stirred at room temperature overnight and diluted with ice. The resultant aqueous mixture is filtered to give the title product as a yellow solid (9.9 g, mp 119°–122° C.).

EXAMPLE 27

Preparation of the Oxime of 2'-methoxy-2-(methylthio)-5-nitrobenzophenone

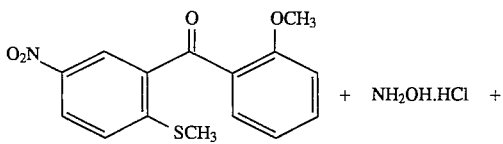

-continued

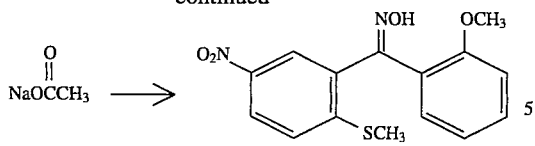

A mixture of 2'-methoxy-2-(methylthio)-5-nitrobenzophenone (8.8 g, 29.0 mmol), sodium acetate (5.25 g, 64.0 mmol) and hydroxylamine hydrochloride (2.2 g, 31.7 mmol) in methanol is refluxed for 2 hours, treated with additional hydroxylamine hydrochloride (10 g) and sodium acetate (5 g), refluxed for an additional 38 hours and poured into an ice/water mixture. The resultant aqueous mixture is filtered to give the title product as a pale yellow solid (8.9 g, mp 198°–203° C.).

EXAMPLE 28

Preparation of
3-(o-Methoxyphenyl)-5-nitro-1,2-benzisothiazole

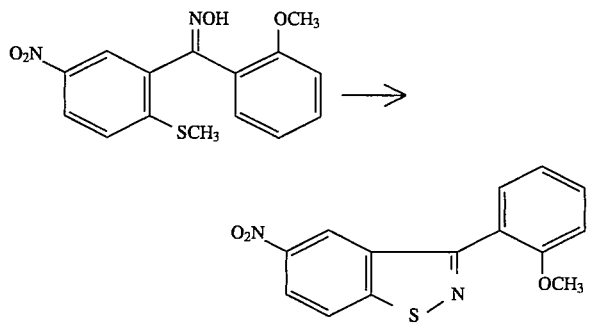

A solution of the oxime of 2'-methoxy-2-(methylthio)-5-nitrobenzophenone (8.3 g, 26.1 mmol) and acetic anhydride (20 mL) in pyridine (150 mL) is refluxed for 5 days, cooled and concentrated in vacuo to obtain a dark solid. A mixture of the solid in methanol is acidified with concentrated hydrochloric acid (pH5), diluted with water and filtered to obtain a solid. A solution of the solid in methylene chloride is passed through a silica gel pad and concentrated in vacuo to give the title product as a solid, mp 193°–198° C.

EXAMPLE 29

Postemergence herbicidal evaluation of test compounds

The postemergence herbicidal activity of the compounds of the present invention is demonstrated by the following tests, wherein a variety of dicotyledonous and monocotyledonous plants are treated with test compounds, dispersed in aqueous acetone mixtures. In the tests, seedling plants are grown in jiffy flats for about two weeks. The test compounds are dispersed in 50/50 acetone/water mixtures containing 0.5% TWEEN®20, a polyoxyethylene sorbitan monolaurate surfactant of Atlas Chemical Industries, in sufficient quantities to provide the equivalent of about 0.125 kg to 1.000 kg per hectare of test compound when applied to the plants through a spray nozzle operating at 40 psi for a predetermined time. After spraying, the plants are placed on greenhouse benches and are cared for in the usual manner, commensurate with conventional greenhouse practices.

From four to five weeks after treatment, the seedling plants are examined and rated according to the rating system set forth below. Data obtained are reported in Table I below. When more than one test is involved for a given compound, the data are averaged.

Plant species employed in these evaluations are reported by header abbreviation, common name and scientific name.

Compounds employed in this postemergence herbicidal evaluation and in the preemergence evaluation in the following example are given a compound number and identified by name. Data in Table I are reported by compound number.

Herbicide Rating Scale

Results of herbicide evaluation are expressed on a rating scale (0–9). The scale is based upon a visual observation of plant stand, vigor, malformation, size, chlorosis and overall plant appearance as compared with a control.

| Rating | Meaning | % Control Compared to Check |
|---|---|---|
| 9 | Complete Kill | 100 |
| 8 | Approaching Complete Kill | 91–99 |
| 7 | Good Herbicidal Effect | 80–90 |
| 6 | Herbicidal Effect | 65–79 |
| 5 | Definite Injury | 45–64 |
| 4 | Injury | 30–44 |
| 3 | Moderate Effect | 16–29 |
| 2 | Slight Effect | 6–15 |
| 1 | Trace Effect | 1–5 |
| 0 | No Effect | 0 |
| — | No Evaluation | |

| PLANT SPECIES EMPLOYED IN HERBICIDAL EVALUATIONS | | |
|---|---|---|
| Header Abb. | Common Name | Scientific Name |
| ABUTH | Velvetleaf | ABUTILON THEOPHRASTI, MEDIC. |
| AMARE | Pigweed, Redroot | AMARANTHUS RETROFLEXUS, L. |
| AMBEL | Ragweed, Common | AMBROSIA ARTEMISIIFOLIA, L. |
| IPOHE | Morningglory, Ivyleaf | IPOMOEA HEDERACEA, (L) JACQ. |
| IPOSS | Morningglory Spp. | IPOMOEA SPP. |
| DIGSA | Crabgrass, (Hairy) L | DIGITARIA SANGUINALIS, (L) SCOP |
| ECHCG | Barnyardgrass | ECHINOCHLOA CRUS-GALLI, (L) BEAU |
| SETVI | Foxtail, Green | SETARIA VIRIDIS, (L) BEAUV |
| GLXMAW | Soybean, Williams | GLYCINE MAX(L)MERR. CV. WILLIAMS |
| ORYSAT | Rice, Tebonnet | ORYZA SATIVA, L. TEBONNET |
| ORYSA | Rice (Unspecified) | ORYZA SATIVA L. (Unspecified) |

| COMPOUNDS EVALUATED AS HERBICIDAL AGENTS | |
|---|---|
| Compound Number | |
| 1 | Methyl 5-(1-cyclohexene-1,2-dicarboximido)-1,2-benzisothiazole-3-acetate |

COMPOUNDS EVALUATED AS HERBICIDAL AGENTS

| Compound Number | |
|---|---|
| 2 | Methyl 5-(1-cyclohexene-1,2-dicarboximido)-α-methyl-1,2-benzisothiazole-3-acetate |
| 3 | N-[3-(o-Methoxyphenyl)-1,2-benzisothiazol-5-yl]-1-cyclohexene-1,2-dicarboximide |
| 4 | Methyl 2-{[6-chloro-5-(1-cyclohexene-1,2-dicarboximido)-1,2-benzisoxazol-3-yl]oxy}-propionate |
| 5 | Methyl 5-(1-cyclohexene-1,2-dicarboximido)-1,2-benzisoxazole-3-acetate |
| 6 | Methyl 2-{[5-(1-cyclohexene-1,2-dicarboximido)-1,2-benzisoxazol-3-yl]oxy}propionate |
| 7 | N-[3-(2-Propynyloxy)-1,2-benzisoxazol-5-yl]-1-cyclohexene-1,2-dicarboximide |
| 8 | N-(3-Hydroxy-1,2-benzisoxazol-5-yl)-1-cyclohexene-1,2-dicarboximide |
| 9 | N-[3-(Allyloxy)-1,2-benzisoxazol-5-yl]-1-cyclohexene-1,2-dicarboximide |
| 10 | Methyl 5-(1-cyclohexene-1,2-dicarboximido)-6-fluoro-1,2-benzisoxazole-3-acetate |
| 11 | Methyl {[5-(1-cyclohexene-1,2-dicarboximido)-6-fluoro-1,2-benzisoxazol-3-yl]oxy}acetate |
| 12 | Methyl 5-(1-cyclohexene-1,2-dicarboximido-6-fluoro-α-methyl-1,2-benzisoxazole-3-acetate |
| 13 | Methyl 5-(3,4-dimethyl-2,5-dioxo-3-pyrrolin-1-yl)-6-fluoro-a-methyl-1,2-benzisoxazole-3-acetate |
| 14 | Methyl {o-[5-(1-cyclohexene-1,2-dicarboximido)-1,2-benzisoxazol-3-yl]phenoxy}acetate |

TABLE I

Postemergence Herbicidal Evaluations of Test Compounds

| Compound Number | Rate (kg/ha) | ABUTH | AMARE | AMBEL | IPOHE | IPOSS | DIGSA | ECHCG | SETVI | GLXMAW | ORYSAT | ORYSA |
|---|---|---|---|---|---|---|---|---|---|---|---|---|
| 1 | 0.500 | 9.0 | 9.0 | 9.0 | 9.0 | — | 5.0 | 5.0 | 5.0 | 6.0 | — | 5.0 |
|   | 0.250 | 9.0 | 9.0 | 9.0 | 8.0 | — | 2.0 | 3.0 | 2.0 | 4.0 | — | 4.0 |
|   | 0.125 | 9.0 | 9.0 | 8.0 | 9.0 | — | 2.0 | 2.0 | 2.0 | 4.0 | — | 3.0 |
| 2 | 0.500 | 9.0 | 9.0 | 9.0 | 9.0 | — | 7.0 | 8.0 | 6.0 | 5.0 | — | 6.0 |
|   | 0.250 | 9.0 | 9.0 | 9.0 | 9.0 | — | 6.0 | 6.0 | 5.0 | 6.0 | — | 6.0 |
|   | 0.125 | 9.0 | 9.0 | 9.0 | 9.0 | — | 5.0 | 5.0 | 3.0 | 5.0 | — | 5.0 |
| 3 | 0.500 | 9.0 | — | 5.0 | — | 8.0 | 2.0 | 2.0 | 3.0 | 7.5 | 4.0 | — |
|   | 0.250 | 9.0 | — | 5.0 | — | 9.0 | 2.0 | 2.0 | 3.0 | 8.0 | 3.5 | — |
|   | 0.125 | 9.0 | — | 6.0 | — | 6.0 | 2.0 | 1.0 | 2.0 | 6.5 | 3.0 | — |
| 4 | 0.500 | 9.0 | 2.0 | 4.0 | — | 9.0 | 0.0 | 1.0 | 2.0 | 3.0 | — | — |
|   | 0.250 | 8.0 | 2.0 | 4.0 | — | 8.0 | 0.0 | 0.0 | 0.0 | 3.0 | — | — |
|   | 0.125 | 7.0 | 2.0 | 2.0 | — | 6.0 | 0.0 | 0.0 | 0.0 | 1.0 | — | — |
| 5 | 0.500 | — | 0.0 | 0.0 | — | 6.0 | 0.0 | 0.0 | 0.0 | 0.0 | 0.0 | — |
|   | 0.250 | — | 0.0 | 0.0 | — | 3.0 | 0.0 | 0.0 | 0.0 | 0.0 | 0.0 | — |
|   | 0.125 | — | 0.0 | 0.0 | — | 0.0 | 0.0 | 0.0 | 0.0 | 0.0 | 0.0 | — |
| 6 | 0.500 | — | 9.0 | 7.0 | — | 7.0 | 3.0 | 2.0 | 2.0 | 4.0 | 4.0 | — |
|   | 0.250 | — | 9.0 | 6.0 | — | 9.0 | 3.0 | 2.0 | 2.0 | 4.0 | 4.0 | — |
|   | 0.125 | — | 8.0 | 6.0 | — | 7.0 | 2.0 | 0.0 | 1.0 | 3.0 | 3.0 | — |
| 7 | 0.500 | 5.0 | 9.0 | 1.0 | — | 6.0 | 3.0 | 3.0 | 2.0 | 2.0 | 2.0 | — |
|   | 0.250 | 3.0 | 9.0 | 1.0 | — | 3.0 | 2.0 | 2.0 | 2.0 | 2.0 | 1.0 | — |
|   | 0.125 | 3.0 | 4.0 | 1.0 | — | 3.0 | 1.0 | 2.0 | 1.0 | 1.0 | 1.0 | — |
| 8 | 1.000 | 2.0 | — | 4.0 | — | 9.0 | 0.0 | 0.0 | 0.0 | 0.0 | — | 4.0 |
|   | 0.500 | 0.0 | — | 2.0 | — | 0.0 | 7.0 | 0.0 | 0.0 | 0.0 | — | 4.0 |
| 9 | 0.500 | 5.0 | 9.0 | 7.0 | 8.0 | — | 4.0 | 3.0 | 2.0 | 3.0 | — | 3.0 |
|   | 0.250 | 5.0 | 9.0 | 6.0 | 8.0 | — | 2.0 | 2.0 | 3.0 | 2.0 | — | 2.0 |
|   | 0.125 | 5.0 | 9.0 | 4.0 | 6.0 | — | 1.0 | 1.0 | 1.0 | 2.0 | — | 2.0 |
| 10 | 0.500 | 9.0 | 9.0 | 8.0 | 9.0 | — | 6.0 | 5.0 | 4.0 | 6.0 | — | 6.0 |
|   | 0.250 | 8.0 | 9.0 | 8.0 | 9.0 | — | 3.0 | 4.0 | 3.0 | 5.0 | — | 5.0 |
|   | 0.125 | 9.0 | 9.0 | 9.0 | 9.0 | — | 4.0 | 5.0 | 3.0 | 3.0 | — | 4.0 |
| 11 | 0.500 | 9.0 | 9.0 | 9.0 | 9.0 | — | 6.0 | 6.0 | 5.0 | 7.0 | — | 5.0 |
|   | 0.250 | 6.0 | 9.0 | 7.0 | 9.0 | — | 4.0 | 5.0 | 4.0 | 6.0 | — | 5.0 |
|   | 0.125 | 6.0 | 9.0 | 7.0 | 9.0 | — | 2.0 | 2.0 | 2.0 | 5.0 | — | 3.0 |
| 12 | 0.500 | 9.0 | 9.0 | 9.0 | 9.0 | — | 7.0 | 8.0 | 7.5 | 6.0 | — | 8.0 |
|   | 0.250 | 9.0 | 9.0 | 9.0 | 9.0 | — | 7.0 | 7.0 | 7.0 | 6.0 | — | 6.0 |
|   | 0.125 | 9.0 | 9.0 | 9.0 | 8.0 | — | 2.0 | 7.0 | 5.5 | 5.0 | — | 4.0 |
| 13 | 0.500 | 9.0 | 8.0 | 8.0 | 7.0 | — | 2.0 | 2.0 | 5.0 | 3.0 | — | 2.0 |
|   | 0.250 | 8.0 | 4.0 | 6.0 | 8.0 | — | 2.0 | 2.0 | 4.5 | 3.0 | — | 2.0 |
|   | 0.125 | 6.0 | 4.0 | 5.0 | 6.0 | — | 1.0 | 2.0 | 3.5 | 3.0 | — | 2.0 |
| 14 | 0.500 | 9.0 | 9.0 | 9.0 | 9.0 | — | 5.0 | 6.0 | 4.0 | 6.0 | — | 4.0 |
|   | 0.250 | 8.0 | 9.0 | 9.0 | 9.0 | — | 5.0 | 5.0 | 2.0 | 5.0 | — | 3.0 |
|   | 0.125 | 8.0 | 9.0 | 8.0 | 8.0 | — | 3.0 | 3.0 | 2.0 | 5.0 | — | 2.0 |

EXAMPLE 30

Preemergence herbicidal evaluation of test compounds

The preemergence herbicidal activity of the test compounds of the present invention is exemplified by the following tests in which the seeds of a variety of monocotyledonous and dicotyledonous plants are separately mixed with potting soil and planted on top of approximately one inch of soil in separate pint cups. After planting, the cups are sprayed with the selected aqueous acetone solution containing test compound in sufficient quantity to provide the equivalent of about 0.50 to 4.0 kg per hectare of test compound per cup. The treated cups are then placed on greenhouse benches, watered and cared for in accordance with conventional greenhouse procedures. From four to five weeks after treatment, the tests are terminated and each cup is examined and rated according to the rating system provided in Example 29.

The data obtained are reported in Table II below. The compounds evaluated are reported by compound number given in Example 29.

effect rated according to the rating system provided in Example 29. The data obtained are reported in Table III.

Preemergence herbicidal activity under flooded paddy conditions is determined as follows: plant seeds or propagating organs are planted in the top 0.5 cm of silt loam soil in 32 oz. plastic containers with a diameter of 10.5 cm and no drainage holes. Water is added to these containers and maintained at 1.5 to 3 cm above the soil surface for the duration of the experiment. The test compounds are applied as aqueous/acetone mixtures 50/50 v/v pipetted directly into the flood water to give the equivalent of 1.0, 0.5, 0.25, 0.125 and 0.063 kg/ha of active ingredient. The treated containers are placed on greenhouse benches and cared for according to normal greenhouse procedures. Three to four weeks after treatment the test is terminated and each container is examined and herbicidal effect rated according to the rating system provided in Example 29. The data obtained are reported in Table III.

Plant species employed in this example are reported by header abbreviation, common name and scientific name.

TABLE II

Preemergence Herbicidal Evaluations of Test Compounds

| Compound Number | Rate (kg/ha) | ABUTH | AMARE | AMBEL | IPOHE | IPOSS | DIGSA | ECHCG |
|---|---|---|---|---|---|---|---|---|
| 1  | 0.500 | 0.0 | 9.0 | 2.0 | 0.0 | —   | 0.0 | 0.0 |
| 2  | 0.500 | 9.0 | 9.0 | 8.0 | 2.0 | —   | 7.0 | 5.0 |
| 4  | 0.500 | 0.0 | 0.0 | 0.0 | —   | 0.0 | 0.0 | 0.0 |
| 5  | 0.500 | 0.0 | 0.0 | 0.0 | —   | 0.0 | 0.0 | 0.0 |
| 6  | 0.500 | 0.0 | 0.0 | 0.0 | —   | 0.0 | 0.0 | 0.0 |
| 7  | 4.00  | 9.0 | —   | 0.0 | —   | 0.0 | 0.0 | 0.0 |
| 8  | 1.00  | 0.0 | 0.0 | 0.0 | —   | 0.0 | 0.0 | 0.0 |
| 9  | 0.500 | 0.0 | 0.0 | 0.0 | 0.0 | —   | 0.0 | 0.0 |
| 10 | 0.500 | 0.0 | 0.0 | 0.0 | 0.0 | —   | 0.0 | 0.0 |
|    | 0.125 | 9.0 | 0.0 | 2.0 | 0.0 | —   | 0.0 | 0.0 |
| 11 | 0.500 | 0.0 | 0.0 | 0.0 | 0.0 | —   | 0.0 | 0.0 |
| 12 | 1.00  | 9.0 | —   | 9.0 | 9.0 | 9.0 | 3.0 | 4.0 |
|    | 0.500 | 9.0 | 9.0 | 8.0 | 5.0 | —   | 0.0 | 0.0 |
| 13 | 1.00  | 9.0 | —   | 4.0 | 5.0 | 6.0 | 2.0 | 0.0 |
|    | 0.500 | 0.0 | 0.0 | 0.0 | 0.0 | —   | 0.0 | 0.0 |
| 14 | 0.500 | 3.0 | 5.0 | 9.0 | 0.0 | —   | 0.0 | 0.0 |

EXAMPLE 31

Rice tolerance to post-transplant applications and preemergence weed control under flooded paddy conditions The tolerance of transplanted rice to post-transplanted herbicide applications is determined as follows: two ten-day-old rice seedlings (CV. Tebonnet) are transplanted into a silt loam soil in 32 oz. plastic containers with a diameter of 10.5 cm and no drainage holes. After transplanting the containers are flooded and the water level is maintained at 1.5 to 3 cm above the soil surface. Three days after transplanting, the flooded soil surface of the containers is treated with the selected aqueous/acetone 50/50 v/v mixture containing the test compounds to provide the equivalent of 1.0, 0.5, 0.25, 0.125 and 0.063 kg/ha of active ingredient. The treated containers are placed on greenhouse benches, watered such that the water level is maintained as stated above, and cared for according to normal greenhouse procedures. Three to four weeks after treatment the test is terminated and each container is examined and herbicidal

| PLANT SPECIES EMPLOYED IN RICE TOLERANCE/ PREEMERGENCE WEED CONTROL EVALUATIONS | | |
|---|---|---|
| Header Abb. | Common Name | Scientific Name |
| ECHORC | Watergrass (Calif.) | ECHINOCHLOA ORYZOIDES (ARD.) FRITSCH |
| CYPIR | Rice Flatsedge | CYPERUS IRIA |
| CYPSE | Flatsedge | CYPERUS SEROTINUS, ROTTB. |
| MOOVA | Monochoria | MONOCHORIA VAGINALIS, PRESL. |
| SAGPY | Arrowhead (pygmaea) | SAGITTARIA PYGMAEA, L. |
| ORYSAT | Rice, Tebonnet | ORYZA SATIVA, L. TEBONNET |

As can be seen from the data in Table III, N-[3-(o-methoxyphenyl)-1,2-benzisothiazol-5-yl]-1-cyclohexene-1,2-dicarboximide is useful for the preemergence control of watergrass, rice flatsedge, flatsedge and monochoria in the presence of transplanted rice.

TABLE III

| | PADDY CONDITIONS - POST-TRANSPLANT RICE PREEMERGENCE WEEDS | | | | | | |
|---|---|---|---|---|---|---|---|
| Compound | Rate (kg/ha) | ECHORC | CYPIR | CYPSE | MOOVA | SAGPY | ORYSAT |
| N-[3-(o-methoxyphenyl)-1,2-benz- | 1.000 | 9.0 | 9.0 | 9.0 | 9.0 | 4.0 | 1.0 |
| isothiazol-5-yl]-1-cyclohexene- | 0.500 | 7.0 | 9.0 | 9.0 | 9.0 | 2.0 | 0.0 |
| 1,2-dicarboximide | 0.250 | 7.0 | 9.0 | 2.0 | 9.0 | 0.0 | 0.0 |
| | 0.125 | 4.0 | 9.0 | 0.0 | 9.0 | 0.0 | 0.0 |
| | 0.063 | 2.0 | 8.0 | 0.0 | 8.0 | 0.0 | 0.0 |

What is claimed is:

1. A compound having the structural formula

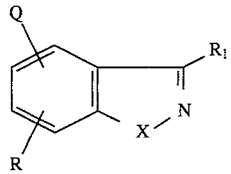

wherein

R is hydrogen, halogen, $C_1$–$C_4$alkyl, $C_1$–$C_4$haloalkyl, $C_1$–$C_4$alkoxy or $C_1$–$C_4$haloalkoxy;

$R_1$ is halogen, $X_1R_2$ or $R_2$;

X is O, and $X_1$ is O or S;

$R_2$ is hydrogen, $C_1$–$C_4$alkyl optionally substituted with one to three halogen atoms, one to three $C_1$–$C_4$alkoxy groups, one to three $C_1$–$C_4$alkylthio groups, one cyano group, one $COR_3$ group, one $CO_2R_4$ group, one $CONR_5R_6$ group or one phenyl group optionally substituted with one to three halogen atoms, one to three $C_1$–$C_4$alkyl groups, one to three $C_1$–$C_4$alkoxy groups, one $C_3$–$C_6$cycloalkyl group, one $C_1$–$C_4$haloalkyl group, one $C_1$–$C_4$alkylthio group, one cyano group, one nitro group, one $COR_7$ group, one $CO_2R_8$ group or one $OR_9$ group, $C_3$–$C_7$cycloalkyl optionally substituted with one to three halogen atoms, one to three $C_1$–$C_4$alkoxy groups, one to three $C_1$–$C_4$alkylthio groups, one cyano group, one $COR_3$ group, one $CO_2R_4$ group, one $CONR_5R_6$ group or one phenyl group optionally substituted with one to three halogen atoms, one to three $C_1$–$C_4$alkyl groups, one to three $C_1$–$C_4$alkoxy groups, one $C_3$–$C_6$cycloalkyl group, one $C_1$–$C_4$haloalkyl group, one $C_1$–$C_4$alkylthio group, one cyano group, one nitro group, one $COR_7$ group, one $CO_2R_8$ group or one $OR_9$ group, $C_2$–$C_6$alkenyl optionally substituted with one to three halogen atoms, one to three $C_1$–$C_4$alkoxy groups, one to three $C_1$–$C_4$alkylthio groups, one cyano group, one $COR_3$ group, one $CO_2R_4$ group, one $CONR_5R_6$ group or one phenyl group optionally substituted with one to three halogen atoms, one to three $C_1$–$C_4$alkyl groups, one to three $C_1$–$C_4$alkoxy groups, one $C_3$–$C_6$cycloalkyl group, one $C_1$–$C_4$haloalkyl group, one $C_1$–$C_4$alkylthio group, one cyano group, one nitro group, one $COR_7$ group, one $CO_2R_8$ group or one $OR_9$ group, $C_4$–$C_7$cycloalkenyl optionally substituted with one to three halogen atoms, one to three $C_1$–$C_4$alkoxy groups, one to three $C_1$–$C_4$alkylthio groups, one cyano group, one $COR_3$ group, one $CO_2R_4$ group, one $CONR_5R_6$ group or one phenyl group optionally substituted with one to three halogen atoms, one to three $C_1$–$C_4$alkyl groups, one to three $C_1$–$C_4$alkoxy groups, one $C_3$–$C_6$cycloalkyl group, one $C_1$–$C_4$haloalkyl group, one $C_1$–$C_4$alkylthio group, one cyano group, one nitro group, one $COR_7$ group, one $CO_2R_8$ group or one $OR_9$ group, $C_2$–$C_6$alkynyl optionally substituted with one to three halogen atoms, one to three $C_1$–$C_4$alkoxy groups, one to three $C_1$–$C_4$alkylthio groups, one cyano group, one $COR_3$ group, one $CO_2R_4$ group, one $CONR_5R_6$ group or one phenyl group optionally substituted with one to three halogen atoms, one to three $C_1$–$C_4$alkyl groups, one to three $C_1$–$C_4$alkoxy groups, one $C_3$–$C_6$cycloalkyl group, one $C_1$–$C_4$haloalkyl group, one $C_1$–$C_4$alkylthio group, one cyano group, one nitro group, one $COR_7$ group, one $CO_2R_8$ group or one $OR_9$ group, or phenyl optionally substituted with one to three halogen atoms, one to three $C_1$–$C_4$alkyl groups, one to three $C_1$–$C_4$alkoxy groups, one $C_3$–$C_6$cycloalkyl group, one $C_1$–$C_4$haloalkyl group, one $C_1$–$C_4$alkylthio group, one cyano group, one nitro group, one $COR_3$ group, one $CO_2R_4$ group or one $OR_9$ group;

$R_3$, $R_5$, $R_6$ and $R_7$ are each independently hydrogen, $C_1$–$C_4$alkyl, $C_2$–$C_4$alkenyl, $C_2$–$C_4$alkynyl, benzyl or phenyl;

$R_9$ is $C_1$–$C_4$alkyl substituted with one $CO_2R_{10}$ group;

$R_4$, $R_8$ and $R_{10}$ are each independently hydrogen, $C_1$–$C_4$alkyl, $C_2$–$C_4$alkenyl, $C_2$–$C_4$alkynyl, benzyl, phenyl or an alkali metal, alkaline earth metal, manganese, copper, zinc, cobalt, silver or nickel cation;

Q is selected from

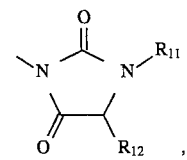 Q1

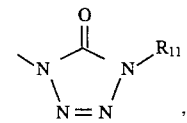 Q2

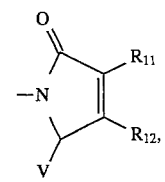 Q3

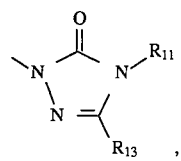 Q4
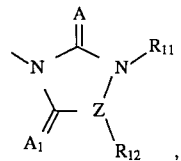 Q5
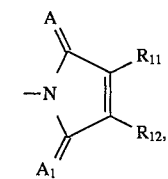 Q6
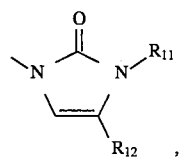 Q7
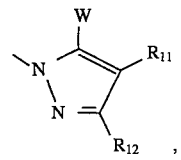 Q8
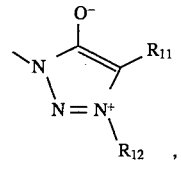 Q9
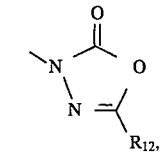 Q10
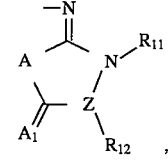 Q11
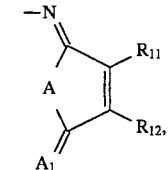 Q12
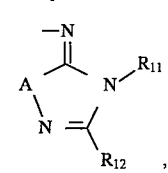 Q13
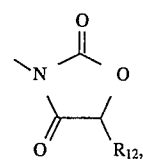 Q14
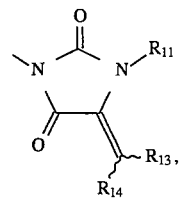 Q15
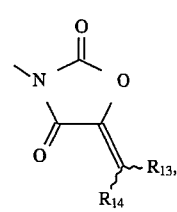 Q16
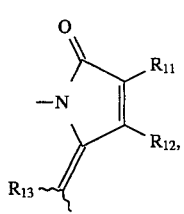 Q17
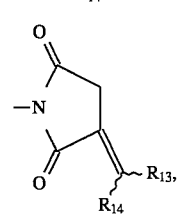 Q18
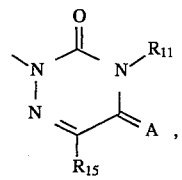 Q19
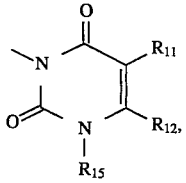 Q20
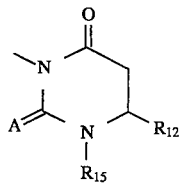 Q21
or

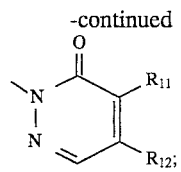

Q22

$R_{11}$ and $R_{12}$ are each independently hydrogen,
$C_1$–$C_6$alkyl optionally substituted with one or more halogen atoms, or
$C_3$–$C_6$cycloalkyl optionally substituted with one or more halogen atoms, and
when $R_{11}$ and $R_{12}$ are taken together with the atoms to which they are attached, they represent a four- to seven-membered saturated or unsaturated ring optionally interrupted by O, S or N, and optionally substituted with one to three methyl groups or one or more halogen atoms;

$R_{13}$, $R_{14}$ and $R_{15}$ are each independently hydrogen or $C_1$–$C_3$alkyl;

A and $A_1$ are each independently O or S;

V is hydroxy, halogen, $C_1$–$C_3$alkoxy or $C_1$–$C_3$alkylthio;

W is halogen or $C_1$–$C_3$alkyl; and

Z is N or CH.

2. The compound according to claim 1 methyl {o-[5-(1-cyclohexene-1,2-dicarboximido)-1,2-benzisoxazol-3-yl]phenoxy}acetate.

3. The compound according to claim 1 methyl 5-(1-cyclohexene-1,2-dicarboximido)-6-fluoro-1,2-benzisoxazole-3-acetate.

4. The compound according to claim 1 methyl 5-(1-cyclohexene-1,2-dicarboximido)-6-fluoro-α-methyl-1,2-benzisoxazole-3-acetate.

5. The compound according to claim 1 methyl 5-(3,4-dimethyl-2,5-dioxo-3-pyrrolin-1-yl)-6-fluoro-α-methyl-1,2-benzisoxazole-3-acetate.

6. The compound according to claim 1 N-[3-(allyloxy)-1,2-benzisoxazol-5-yl]-1-cyclohexene-1,2-dicarboximide.

7. The compound according to claim 1 methyl 2-{[6-chloro-5-(1-cyclohexene-1,2-dicarboximido)-1,2-benzisoxazol-3-yl]oxy}propionate.

* * * * *